US009765294B2

(12) United States Patent
Dehottay et al.

(10) Patent No.: US 9,765,294 B2
(45) Date of Patent: Sep. 19, 2017

(54) **CHEMICALLY DEFINED MEDIUM FOR THE INDUSTRIAL SCALE CULTURE OF A SPECIES OF *BORDETELLA***

(71) Applicant: GLAXOSMITHKLINE BIOLOGICALS, S.A., Rixensart (BE)

(72) Inventors: Philippe Marc Helene Dehottay, Rixensart (BE); Philippe Goffin, Rixensart (BE); Filipe Branco dos Santos, Amsterdam (NL); Bas Teusink, Amsterdam (NL)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 15/021,345

(22) PCT Filed: Sep. 11, 2014

(86) PCT No.: PCT/IB2014/064428

§ 371 (c)(1),
(2) Date: Mar. 11, 2016

(87) PCT Pub. No.: WO2015/036953

PCT Pub. Date: Mar. 19, 2015

(65) Prior Publication Data

US 2016/0222344 A1 Aug. 4, 2016

(30) Foreign Application Priority Data

Sep. 13, 2013 (GB) .................................. 1316351.4

(51) Int. Cl.
*C12N 1/20* (2006.01)

(52) U.S. Cl.
CPC ..................................... *C12N 1/20* (2013.01)

(58) Field of Classification Search
None
See application file for complete search history.

(56) References Cited

U.S. PATENT DOCUMENTS

| | | | | |
|---|---|---|---|---|
| 4,500,639 | A * | 2/1985 | Suzuki | C12N 1/20 435/243 |
| 5,338,670 | A * | 8/1994 | Sekura | C07K 14/235 435/244 |
| 2013/0288340 | A1* | 10/2013 | Tanaka | C12N 1/14 435/245 |

FOREIGN PATENT DOCUMENTS

| | | |
|---|---|---|
| EP | 0 077 646 | 4/1983 |
| WO | 2012/090554 | 7/2012 |

OTHER PUBLICATIONS

Stainer D. et al. A Simple Chemically Defined Medium for the Production of Phase I Bordetella pertussis. J of General Microbiology 63:211-220, 1971.*
Lothe R. et al. Stainer and Scholte's pertussis Medium with an Alternative Buffer. J of Biological Standardization 13(2)129-134, 1985.*
Imaizumi A. et al. Heptakis(2,6-O-Dimethyl)Beta-Cyclodextrin: A Novel Growth Stimulant for Bordetella pertussis Phase I. J of Clinical Microbiology 17(5)781-786, May 1983.*
Lacey B. Antigenic Modulation of Bortetella pertussis. J Hyg 58:57-93, 1960.*
Schneider and Parker, Effect of Pyridines on Phenotypic Properties of Bordetella pertussis, Infect & Immun (1982) 38(2):548-553.

* cited by examiner

*Primary Examiner* — Ralph Gitomer
(74) *Attorney, Agent, or Firm* — Virginia G. Campen

(57) ABSTRACT

Chemically defined media for the industrial-scale culture of *Bordetella* species.

18 Claims, 2 Drawing Sheets

Figure 1:
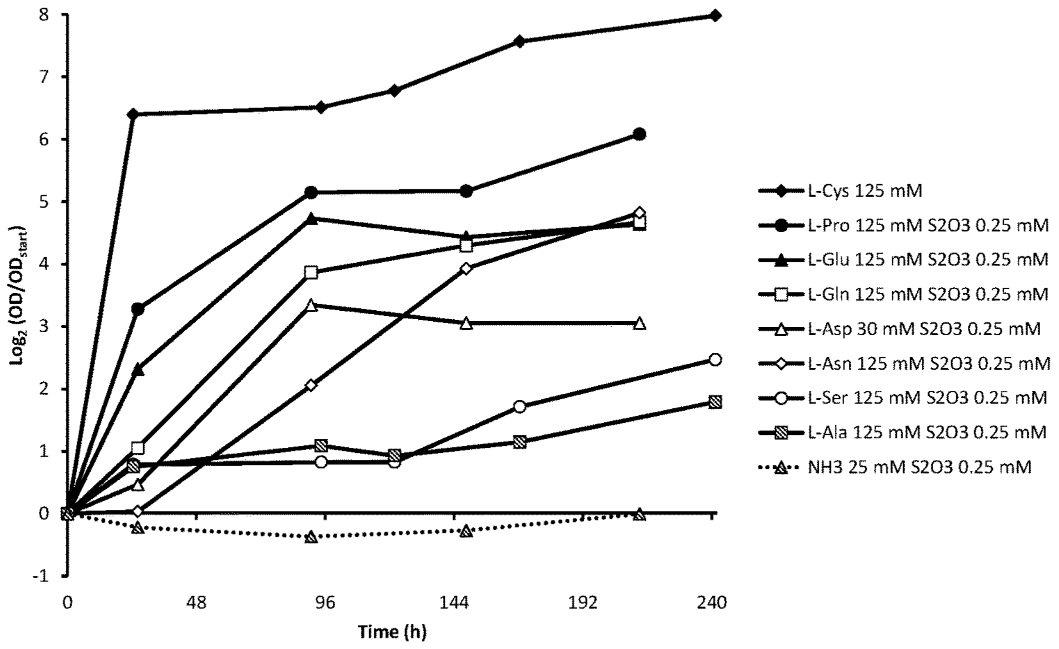

CHEMICALLY DEFINED MEDIUM FOR THE INDUSTRIAL SCALE CULTURE OF A SPECIES OF *BORDETELLA*

This application is filed pursuant to 35 U.S.C. §371 as a United States National Phase Application of International Patent Application Serial No. PCT/IB2014/064428 filed Sep. 11, 2014, which claims priority to United Kingdom Application No. GB 1316351.4 filed Sep. 13, 2013, and the entire contents of each of the foregoing applications are hereby incorporated by reference.

BACKGROUND

The genus *Bordetella* is the causative agent for a number of bacterial diseases, for example *Bordetella pertussis* (also known as *Haemophilus pertussis*) is responsible for whooping cough, a respiratory disease that can be severe in infants and young children. The clinical course of the disease is characterised by paroxysms of rapid coughs followed by inspiratory effort, often associated with a characteristic 'whooping' sound. In serious cases, oxygen deprivation can lead to brain damage; however the most common complication is secondary pneumonia.

Whooping cough is usually considered to be caused by *B. pertussis*, but occasionally *B. parapertussis* is isolated from patients with typical signs and symptoms of whooping cough. *B. parapertussis* infection is of lower frequency than *B. pertussis* with 5-10% of whooping cough being associated with *B. parapertussis* (Mertsola (1985) Eur J Clin Microbiol 4; 123; Lautrop (1971) Lancet 1(7711) 1195-1198). *B. parapertussis* is associated with mild clinical symptoms which, combined with its serological cross-reactivity with *B. pertussis*, makes *B. parapertussis* difficult to diagnose.

The first generation of vaccines against *B. pertussis* were whole cell vaccines, composed of whole killed bacteria. These were introduced in many countries in the 1950s and 1960s and were successful at reducing the incidence of whooping cough. A problem with whole cell *B. pertussis* vaccines is the high level of reactogenicity associated with them. Acellular vaccines containing purified *B. pertussis* proteins are less reactogenic and have been adopted for the vaccination programmes of many countries. Acellular vaccines typically containing pertussis toxin (PT), filamentous haemagglutinin (FHA) and quite often pertactin (PRN), are widely used and provide effective protection from the severity of whooping cough.

*Bordetella* toxins for use in such vaccines are generated by fermenting *Bordetella* and isolating the produced virulence factors, however *Bordetella* species are fastidious organisms which are difficult to grow in high concentrations (Doern *Clin. infect. dis.* 2000, 30 166-173), furthermore it is difficult to express *Bordetella* virulence factors such as FHA (filamentous haemagluttinin), Pertactin (PRN) and Pertusiss Toxin (PT) from *Bordetella pertussis* at high levels.

*Bordetella* can be grown in chemically defined media. For example Stainer and Scholte (Journal of General Microbiology (1971), 63, 211-220) discloses a simple chemically defined medium for the production of *pertussis*. Growth in chemically defined media provides advantages as undefined media can vary in their nutritional content leading to unpredictability in growth and expression.

However chemically defined medium can be expensive and difficult to manufacture in large amounts, in addition it is difficult to design balanced chemically defined media that support high levels of toxin production. The present inventors have surprisingly found that a number of modifications can be made to a chemically defined medium for a species of *Bordetella pertussis* to form simple media which support high levels of virulence factor production.

BRIEF SUMMARY

In a first aspect of the invention there is provided a chemically defined medium for a species of *Bordetella* wherein the chemically defined medium comprises one or more of the following modifications:
(i) the chemically defined medium comprises less than 0.035 mM, less than 0.030 mM, less than 0.020 mM or less than 0.010 mM sulfate;
(ii) the chemically defined medium comprises a source of cysteine selected from the group consisting of cysteine and cystine wherein the source of cysteine is at a concentration of less than 0.50 mM, less than 0.30 mM, less than 0.25 mM, less than 0.20 mM, less than 0.15 mM, less than 0.10 mM, less than 0.05 mM or less than 0.03 mM;
(iii) the chemically defined medium comprises an inorganic source of sulfur selected from the group consisting of thiosulfate, trithionate, tetrathionate, peroxodisulfate, sulphide and sulphite;
(iv) the chemically defined medium does not comprise an organic source of sulfur;
(v) the chemically defined medium comprises a buffer selected from the group consisting of MOPS (3-(N-morpholino)propanesulfonic acid), MES (2-(N-morpholino)ethanesulfonic acid), HEPES (4-(2-hydroxyethyl)-1-piperazineethanesulfonic acid and PIPES (piperazine-N,N'-bis(2-ethanesulfonic acid));
(vi) the chemically defined medium comprises greater than 2 µM, greater than 3 µM, greater than 4 µM, greater than 5 µM than 6 µM copper;
(vii) the chemically defined medium comprises greater than 2 µM, greater than 5 µM, greater than 10 µM, greater than 50 µM, greater than 100 µM or greater than 400 µM magnesium;
(viii) the chemically defined medium comprises a sole amino acid source;
(ix) the chemically defined medium does not comprise a source of amino acids;
(x) the chemically defined medium comprises an additive selected from the group consisting of zinc, cobalt, thiamine, riboflavin and pantothenate;
(xi) the chemically defined medium comprises an additive selected from the group consisting of greater than 0.4 µM biotin, greater than 50 µM calcium, greater than 15 µM niacin, and greater than 25 µM ascorbic acid; or
(xii) the chemically defined medium comprises an amino acid selected from the group consisting of aspartate at a concentration greater than 1000 µM, glycine at a concentration of greater than 1000 µM, methionine at a concentration of greater than 500 µM and leucine at a concentration of greater than 1500 µM.

In a second aspect of the invention there is provided a chemically defined medium for a species of *Bordetella* wherein the chemically defined medium comprises at least two components and wherein the at least two components are selected from the group consisting of:
a) carbon and phosphorus at a ratio of greater than 100:1, greater than 125:1, greater than 150:1, greater than 175:1 or greater than 200:1 (carbon:phosphorus) (mol/mol);
(b) glutamate and phosphorus at a ratio of greater than 20:1, greater than 22:1, greater than 24:1 or greater than 25:1 (glutamate:phosphorus) (mol/mol);

(c) carbon and magnesium at a ratio of less than 600:1, less than 500:1, less than 400:1 or less than 300:1 (carbon: magnesium) (mol/mol);
(d) glutamate and magnesium at a ratio of less than 115:1, less than 110:1, less than 105:1 or less than 100:1 (glutamate:magnesium) (mol/mol);
(e) carbon and copper at a ratio of greater than 3000:1, greater than 3500:1, or greater than 4000:1 (carbon: copper) (mol/mol);
(f) glutamate and copper at a ratio of greater than 170:1, greater than 180:1, greater than 200:1 or greater than 250:1 (glutamate:copper) (mol/mol);
(g) carbon and iron at a ratio of greater than 9500:1, greater than 1000:1, greater than 1250:1 or greater than 1500:1 (carbon:iron) (mol/mol);
(h) glutamate and iron at ratio of greater than 1600:1, greater than 1800:1, greater than 2000:1 or greater than 2500:1 (glutamate:iron) (mol/mol);
(i) carbon and glycine at a ratio of less than 500:1, less than 400:1, less than 300:1 or less than 250:1 (carbon:glycine) (mol/mol);
(j) glutamate and glycine at a ratio of less than 100:1, less than 80:1, less than 75:1 or less than 60:1 (glutamate: glycine) (mol/mol);
(k) carbon and leucine at a ratio of less than 440:1, less than 400:1, less than 350:1 or less than 300:1 (carbon:leucine) (mol/mol);
(l) glutamate and leucine at a ratio of less than 75:1, less than 70:1, less than 60:1 or less than 50:1 (glutamate: leucine) (mol/mol);
(m) carbon and methionine at a ratio of less than 1200:1, less than 1000:1, less than 800:1 or less than 750:1 (carbon: methionine) (mol/mol);
(n) glutamate and methionine at a ratio of less than 200:1, less than 175:1, less than 150:1 or less than 120:1 (glutamate:methionine) (mol/mol);
(o) carbon and calcium at a ratio of greater than 3750:1, greater than 4000:1, greater than 4500:1 or greater than 5000:1 (carbon:calcium) (mol/mol);
(p) glutamate and calcium at a ratio of greater than 620:1, greater than 650:1, greater than 675:1 or greater than 750:1 (glutamate:calcium) (mol/mol);
(q) carbon and cobalt at a ratio of greater than 3000:1, greater than 3500:1, greater than 4750:1 or greater than 5000:1 (carbon:cobalt) (mol/mol);
(r) glutamate and cobalt at a ratio of greater than 750:1, greater than 1000:1, greater than 1250:1 or greater than 1500:1 (glutamate:cobalt) (mol/mol);
(s) carbon and zinc at a ratio of greater than 3000:1, greater than 3500:1, greater than 4000:1 or greater than 5000:1 (carbon:zinc) (mol/mol);
(t) glutamate and zinc at a ratio of greater than 750:1, greater than 1000:1, greater than 1250:1 or greater than 1500:1 (glutamate:zinc) (mol/mol);
(u) carbon and sulfate equivalents at a ratio of greater than 750:1, greater than 1000:1, greater than 1250:1 or greater than 1500:1 (carbon:sulfate equivalents) (mol/mol); and
(v) glutamate and sulfate equivalents at a ratio of greater than 130:1, greater than 150:1, greater than 175:1 or greater than 200:1 (glutamate:sulfate equivalents) (mol/mol).

In a third aspect of the invention there is provided a fermentation process for growing a species of *Bordetella* in a chemically defined medium (CDM) comprising
(a) inoculating the chemically defined medium of the invention with the species of *Bordetella;*
(b) maintaining the species of *Bordetella* in the chemically defined medium for a period of time sufficient to allow biomass accumulation.

In a fourth aspect of the invention there is provided a virulence factor obtainable by the fermentation process of the invention.

In a fifth aspect of the invention there is provided a virulence factor obtained by the fermentation process of the invention.

In a sixth aspect of the invention there is provided an immunogenic composition comprising the virulence factor of the invention.

In a seventh aspect of the invention there is provided a vaccine comprising the immunogenic composition of the invention.

In an eighth aspect of the invention there is provided a use of the immunogenic composition of the invention or the vaccine of the invention in the prevention or treatment of disease.

In a ninth aspect of the invention there is provided a use of the immunogenic composition of the invention or the vaccine of the invention in the preparation of a medicament for the treatment or prevention of bacterial disease.

In a tenth aspect of the invention there is provided a method of preventing or treating disease comprising administering the immunogenic composition of the vaccine to a patient.

DETAILED DESCRIPTION

Chemically Defined Media

Chemically defined media (CDM) are often considered to be beneficial as, unlike non chemically defined media, chemically defined media contain a precise concentration of each nutrient thus reducing variability of the medium and improving the quality of the fermented product. However it can be difficult to create a balanced optimal chemically defined medium as it is difficult to predict the nutrients/medium components required by different bacteria. Ideally the chemically defined medium should be substantially balanced, i.e. on completion of fermentation there should not be an excess of any particular medium component due to the presence of too much of that medium component for the bacteria to metabolise, since balanced media support more effective growth and are more cost-effective. A semi-synthetic medium for *Bordetella pertussis* has been designed by Goldner (J. Gen. Microbiol. (1966), 44, 439-444), however this was too complicated and expensive to be used on industrial scale. Stainer Scholte attempted to design a simpler medium which would be more appropriate for industrial scale fermentation, however this is not optimal for production of virulence factors (Journal of General Microbiology (1971), 63, 211-220). The present inventors have found that certain modifications can be carried out to these chemically defined medium to simplify the media or to significantly increase the yield of virulence factors obtained from *Bordetella* grown in such media.

These modifications include:
(i) the chemically defined medium comprises less than 0.035 mM, less than 0.030 mM, less than 0.020 mM or less than 0.010 mM sulfate;
(ii) the chemically defined medium comprises a source of cysteine selected from the group consisting of cysteine and cystine wherein the source of cysteine is at a concentration of less than 0.50 mM, less than 0.30 mM, less than 0.25 mM, less than 0.20 mM, less than 0.15 mM, less than 0.10 mM, less than 0.05 mM or less than 0.03 mM;

(iii) the chemically defined medium comprises an inorganic source of sulfur selected from the group consisting of thiosulfate, trithionate, tetrathionate, peroxodisulfate, sulphide and sulphite;

(iv) the chemically defined medium does not comprise an organic source of sulfur;

(v) the chemically defined medium comprises a buffer selected from the group consisting of MOPS, MES, HEPES and PIPES;

(vi) the chemically defined medium comprises greater than 2 μM, greater than 3 μM, greater than 4 μM, greater than 5 μM or greater than 6 μM copper;

(vii) the chemically defined medium comprises greater than 2 μM, greater than 5 μM, greater than 10 μM, greater than 50 μM, greater than 100 μM or greater than 400 μM magnesium;

(viii) the chemically defined medium comprises a sole amino acid source;

(ix) the chemically defined medium does not comprise a source of amino acids;

(x) the chemically defined medium comprises an additive selected from the group consisting of zinc, cobalt, thiamine, riboflavin and pantothenate;

(xi) the chemically defined medium comprises an additive selected from the group consisting of greater than 0.4 μM biotin, greater than 50 μM calcium, greater than 15 μM niacin, and greater than 25 μM ascorbic acid; or (xii) the chemically defined medium comprises an amino acid selected from the group consisting of aspartate at a concentration greater than 1000 μM, Glycine at a concentration of greater than 1000 μM, methionine at a concentration of greater than 500 μM and leucine at a concentration of greater than 1500 μM.

Thus in a first aspect of the present invention there is provided a chemically defined medium for a species of *Bordetella* wherein the chemically defined medium comprises one or greater of the above-described modifications.

In addition attempts at formulating new chemically defined media often involve taking a complex medium and replacing the complex medium component (such as casmino casein hydolysate) with the equivalent amounts of individual chemically defined components. However the present inventors have surprisingly found that the ratio between medium components can be very important for ensuring that the chemically defined medium is balanced and supports high yield production of virulence factors.

Thus in a second aspect of the present invention there is provided a chemically defined medium for a species of *Bordetella* wherein the chemically defined medium comprises at least two components and wherein the at least two components are selected from the group consisting of:

(a) carbon and phosphorus at a ratio of greater than 100:1, greater than 125:1, greater than 150:1, greater than 175:1 or greater than 200:1 (carbon:phosphorus) (mol/mol);

(b) glutamate and phosphorus at a ratio of greater than 20:1, greater than 22:1, greater than 24:1 or greater than 25:1 (glutamate:phosphorus) (mol/mol);

(c) carbon and magnesium at a ratio of less than 600:1, less than 500:1, less than 400:1 or less than 300:1 (carbon:magnesium) (mol/mol);

(d) glutamate and magnesium at a ratio of less than 115:1, less than 110:1, less than 105:1 or less than 100:1 (glutamate:magnesium) (mol/mol);

(e) carbon and copper at a ratio of greater than 3000:1, greater than 3500:1, or greater than 4000:1 (carbon:copper) (mol/mol);

(f) glutamate and copper at a ratio of greater than 170:1, greater than 180:1, greater than 200:1 or greater than 250:1 (glutamate:copper) (mol/mol);

(g) carbon and iron at a ratio of greater than 9500:1, greater than 1000:1, greater than 1250:1 or greater than 1500:1 (carbon:iron) (mol/mol);

(h) glutamate and iron at ratio of greater than 1600:1, greater than 1800:1, greater than 2000:1 or greater than 2500:1 (glutamate:iron) (mol/mol);

(i) carbon and glycine at a ratio of less than 500:1, less than 400:1, less than 300:1 or less than 250:1 (carbon:glycine) (mol/mol);

(j) glutamate and glycine at a ratio of less than 100:1, less than 80:1, less than 75:1 or less than 60:1 (glutamate:glycine) (mol/mol);

(k) carbon and leucine at a ratio of less than 440:1, less than 400:1, less than 350:1 or less than 300:1 (carbon:leucine) (mol/mol);

(l) glutamate and leucine at a ratio of less than 75:1, less than 70:1, less than 60:1 or less than 50:1 (glutamate:leucine) (mol/mol);

(m) carbon and methionine at a ratio of less than 1200:1, less than 1000:1, less than 800:1 or less than 750:1 (carbon:methionine) (mol/mol);

(n) glutamate and methionine at a ratio of less than 200:1, less than 175:1, less than 150:1 or less than 120:1 (glutamate:methionine) (mol/mol);

(o) carbon and calcium at a ratio of greater than 3750:1, greater than 4000:1, greater than 4500:1 or greater than 5000:1 (carbon:calcium) (mol/mol);

(p) glutamate and calcium at a ratio of greater than 620:1, greater than 650:1, greater than 675:1 or greater than 750:1 (glutamate:calcium) (mol/mol);

(q) carbon and cobalt at a ratio of greater than 3000:1, greater than 3500:1, greater than 4750:1 or greater than 5000:1 (carbon:cobalt) (mol/mol);

(r) glutamate and cobalt at a ratio of greater than 750:1, greater than 1000:1, greater than 1250:1 or greater than 1500:1 (glutamate:cobalt) (mol/mol);

(s) carbon and zinc at a ratio of greater than 3000:1, greater than 3500:1, greater than 4000:1 or greater than 5000:1 (carbon:zinc) (mol/mol);

(t) glutamate and zinc at a ratio of greater than 750:1, greater than 1000:1, greater than 1250:1 or greater than 1500:1 (glutamate:zinc) (mol/mol);

(u) carbon and sulfate equivalents at a ratio of greater than 750:1, greater than 1000:1, greater than 1250:1 or greater than 1500:1 (carbon:sulfate equivalents) (mol/mol); and (v) glutamate and sulfate equivalents at a ratio of greater than 130:1, greater than 150:1, greater than 175:1 or greater than 200:1 (glutamate:sulfate equivalents) (mol/mol).

The term 'chemically defined medium' refers to a medium which is substantially devoid of complex material such as yeast, casamino acids, peptones, tryptones, yeast extract. See e.g., Jayme and Smith, Cytotechnology 33 (1-3):27-36 (2000). In particular, as used herein, a chemically defined medium does not include casamino acids (CAA) as the source of amino acids in the medium. As used herein, casamino acids refers to a mixture of amino acids obtained by the hydrolysis of casein.

The CDM of the present invention are described in both positive terms (ingredient(s) or component(s) that are included in the medium) as well as negative terms (ingredient(s) or component(s) that are excluded from the medium).

A 'source' is a component of the medium which provides at least one specific ingredient to the medium. E.g., cystine is a source of cysteine as it provides cysteine for use by organisms grown on the medium. As used herein, the ingredient itself is considered a 'source,', e.g., sulfate is a source of sulfate, and cysteine is a source of cysteine, etc. A 'source' may provide more than one ingredient, e.g., an amino acid may be a carbon source and a nitrogen source, as well as an amino acid source.

The term 'medium' refers to a source of nutrients sufficient to allow *Bordetella* to grow to reasonably high densities (for example to a biomass of greater than 1.0 g/L, greater than 1.5 g/L, greater than 2.0 g/L or greater than 2.5 g/L dry cell weight).

The chemically defined medium of the invention is for industrial scale culture of a species of *Bordetella*, the term 'industrial scale culture' refers to culture in a fermentor, in one embodiment industrial scale culture is culture in a fermentor with a working volume of between 5 and 10000 liters, between 10 and 5000 liters, between 20 and 2000 liters, between 50 liters and 1000 liters, greater than or equal to 5 liters, greater than or equal to 10 liters, greater than or equal to 15 liters, greater than or equal to 20 liters, greater than or equal to 25 liters, greater than or equal to 50 liters, greater than or equal to 100 liters, less than or equal to 10000 liters, less than or equal to 5000 liters or less than or equal to 2500 liters. In a further embodiment the 'industrial scale culture' is culture suitable for the production of greater than 10 mg/L, greater than 15 mg/L or greater than 20 mg/L pertussis toxin.

During a fermentation process the chemically defined medium of the invention is added to the fermentor at the beginning of the process, although, optionally further portions of the medium may be added during the fermentation process (for example in fed-batch fermentation); alternatively a medium with a different composition may be added later in the fermentation. Such a medium may also be added continuously into the culture medium for use in systems such as chemostats or retentostats. Preferably the fermentation is a fed-batch fermentation.

The chemically defined medium of the invention preferably supports growth yield of the species of *Bordetella* higher than that supported by Stainer Scholte medium (described in Journal of General Microbiology (1971), 63:211-220). This can be determined by seeding a strain of *Bordetella*, by inoculating a flask or fermentor containing Stainer Scholte medium with a first sample of the strain of *Bordetella* and inoculating a flask or fermentor containing the chemically defined medium to be tested with a second sample of the strain of *Bordetella* (using the same volume as the volume selected for the Stainer Scholte medium). The $OD_{650\ nm}$ should be taken at, multiple two time points) for both the samples, these time points must include a time point which is just after inoculation (referred to as time point A) and a time point which is at the end of growth (referred to as time point B). Note that growth is considered to have ceased when the cell concentration between two consecutive time points (separated by at least 24 h) has not increased by more than 10%.If the difference in $OD_{650\ nm}$ between time point B and time point A is higher for the second sample than for the first sample inoculated in the Stainer Scholte medium, the chemically defined medium to be tested supports growth yield of the species of *Bordetella* higher than that supported by Stainer Scholte medium.

The chemically defined medium preferably supports an average generation time of the *Bordetella* species of less than 15 h, less than 12 h, less than 10 h or less than 9 h. This can be tested using a similar method to that described in the paragraph above, however the average generation time is obtained by dividing the time between the time point A and time point B, by the number of generations between these two time points. The number of generations between time point A and time point B is obtained by calculating the ratio between $OD_{650\ nm}$ at the second time point to the $OD_{650\ nm}$ at the first time point, converted to $Log_2$.

The chemically defined medium preferably supports higher levels of pertussis toxin production than that supported by Stainer Scholte medium. This can be determined by inoculating a flask or fermentor containing Stainer Scholte medium with a first sample of the strain of *Bordetella pertussis* and inoculating a flask or fermentor containing the chemically defined medium to be tested (the same volume as the volume selected for the Stainer Scholte medium) with a second sample of the strain of *Bordetella pertussis*, incubating both samples until growth has ceased and calculating the level of pertussis toxin production in each sample. A method for determined the level of pertussis toxin production is described in example 1. If the level of pertussis toxin production for the second sample is higher than for the first sample the chemically defined medium supports higher levels of pertussis toxin production than that supported by Stainer Scholte medium.

In a preferred embodiment the chemically defined medium of the invention supports the species of *Bordetella* to produce pertussis toxin with a yield of greater than 10 mg/L, or greater than 15 mg/L, more preferably the yield is greater than 20 mg/L. Whether or not a chemically defined medium supports the species of *Bordetella* to produce pertussis toxin with a certain yield can be determined by inoculating the chemically defined medium with a sample of the species of *Bordetella*, and incubating the cells until growth has ceased. At the end of growth the yield of pertussis toxin can be calculated using the method described in example 1.

In one embodiment the chemically defined medium is a substantially balanced medium. A substantially balanced medium is a medium in which, at the end of fermentation, there is no significant excess of any particular nutrient. Whether a chemically defined medium is a substantially balanced medium can be tested by incubating the species of *Bordetella* in the medium until growth ceases and examining the medium supernatant after the growth has ceased. If the metabolic sources (i.e. sources of nitrogen phosphorus and sulfur) are used at a substantially similar rate (within 10% of one another) then the chemically defined medium is balanced. In a preferred embodiment the final concentrations of all the metabolic sources will be around 0 mM.

Generally chemically defined media must contain at least a source of carbon, a source of phosphorus, a source of nitrogen, a source of sulfur and a buffer. The source of nitrogen may be organic or inorganic. The source of nitrogen may be an amino acid or peptide, alternatively the source of nitrogen may be a source of nitrogen which is not an amino acid or peptide, in such a chemically defined medium the chemically defined medium does not comprise an amino acid. In one embodiment the source of nitrogen is inorganic. In one embodiment the nitrogen source comprises or consists of a compound selected from the group consisting of amino acids, urea, polyamines, ammonium (such as ammonium chloride, ammonium sulfate or ammonium nitrate), nucleobases, nucleosides, and nucleotides. In a further embodiment the source of nitrogen comprises or consists of ammonium chloride. The source of carbon may comprise or consist of an amino acid or peptide, or may comprise or consist of a source of carbon which is not an amino acid or peptide; in such a chemically defined medium the chemically defined medium does not comprise an amino acid. As used herein the term 'does not comprise an amino acid' means that the medium 'does not comprise' peptides or proteins either, since peptides or proteins are sources of amino acids. In one embodiment the source of carbon comprises or consists of a compound selected from the group consisting of monosaccharides, disaccharides, polysaccharides, polyols (sugar alcohols) organic acids and amino acids. In a further embodiment the source of carbon comprises or consists of a compound selected from the group consisting of glucose, fructose, sorbose, galactosamine, mannose, sucrose, rhamnose, sorbitol, mannitol, citrate, lactate, acetate, pyruvate, fumarate, succinate, proline and glutamate. In a further embodiment the source of carbon comprises glutamate or proline. In a further embodiment the source of carbon comprises or consists of an organic acid selected from the group consisting of citrate, lactate, acetate, pyruvate, fumurate and succinate.

The chemically defined medium of the invention is for industrial scale culture of a species of *Bordetella*. In one embodiment the medium comprises the species of *Bordetella*. In one embodiment the species of *Bordetella* is a species selected from the group consisting of *Bordetella petrii, Bordetella avium, Bordetella hinzii, Bordetella trematum, Bordetella holmesii, Bordetella parapertussis, Bordetella bronchiseptica* and *Bordetella pertussis* (otherwise known as *Haemophilus pertussis*). Preferably the species of *Bordetella* is selected from the group consisting of *Bordetella parapertussis, Bordetella bronchiseptica* and *Bordetella pertussis*. More preferably the species of *Bordetella* is *Bordetella pertussis.*

Sulfur Sources

In a first embodiment the chemically defined medium comprises less than 0.035 mM, less than 0.030 mM, less than 0.020 mM, less than 0.010 mM sulfate, less than 0.005 mM, less than 0.0001 mM, less than 0.00005 mM, less than 0.00001 mM, between 0.035 mM and 0 mM, between 0.005 mM and 0 mM or between 0.00001 mM and 0 mM. The present inventors have surprisingly found that the removal of sulfate from the chemically defined medium increases the yield of virulence factors such as PT significantly when used in a chemically defined medium for *Bordetella*. WO0178462 and Lacey (1960; J. Hyg. 58:57-93) disclose the idea that sulfate can be an inhibitor of virulence factor production; however the low sulfate media disclosed in WO0178462 contained 0.001 g/L added $FeSO_4$. Thus it is clear that the inventors in WO0178462 considered that the presence of at least a certain amount of $FeSO_4$ was required in order to produce a chemically defined medium to allow growth of *pertussis*. It is noteable that in order to obtain high levels of virulence factors the medium must support both virulence factor production and growth of the *Bordetella* to a suitable biomass, so although it was known that sulfate inhibits virulence factor expression, it was not known that *Bordetella* could be grown to reasonable biomass in the absence of sulfate. It should also be noted that Jebb and Tomlinson (J.Gen.Microbio1.17, 59-68) disclose that sulfate was not sufficient to provide a source of sulfur, this contradicts other art, and later documents citing Jebb and Tomlinson (such as Licary, Siber and Swartz Journal of Biotechnology 1 20 (1991) 117-130) continued to add sulfate to their media. This conclusion is supported by other publications on media for *Bordetella*, in general these publications all seem to require that sulfate be present (for example Stainer Scholte medium as described above contains sulfate). The present inventors, however, have surprisingly found that $FeSO_4$ can be replaced with Fe(III) citrate in order to remove the sulfate (thus reducing inhibition of virulence factor expression), and still provide an effective medium which supports growth of *Bordetella*, and that reducing the concentration of sulfate even lower than that disclosed in WO0178462 provides a significant increase in the yield of virulence factors such as PT. In a further embodiment the chemically defined medium does not comprise sulfate.

The phrase 'does not comprise' a certain substrate such as sulfate refers to a medium in which the creator of the medium has not added a significant amount of that substance. Thus a medium can be considered to 'not comprise' a certain substance if the medium comprises a small amount of that substance, which is, for instance a contaminant. Alternatively a medium can be considered to 'not comprise' a certain substance if the creator of the medium has added a very small amount of that substance which is not sufficient to alter the yield of a virulence factor such as Pertussis Toxin. This can be determined by culturing the species of *Bordetella* in the presence of the small amount of that substance and in the absence of the small amount of that substance and measure the yield of that virulence factor in these two cultures using an ELISA. A suitable ELISA is described in Example 1 (Determination of PT concentration).

In one embodiment, the invention provides a chemically defined medium that comprises a source of cysteine selected from the group consisting of cysteine and cystine wherein the source of cysteine is at a concentration of less than 0.50 mM, less than 0.30 mM, less than 0.25 mM, less than 0.20 mM, less than 0.15 mM, less than 0.10 mM, less than 0.05 mM, less than 0.03 mM, less than 0.01 mM, less than 0.005 mM, less than 0.001 mM, less than 0.0005 mM, less than 0.0001 mM, less than 0.00005 mM or less than 0.00001 mM.

Cysteine is generally used for biomass synthesis by *Bordetella*, however when cysteine is present in higher concentrations it will be catabolised to sulfate (Bogdan et al ((2001); Infect. Immun. 69:6823-6830)). This sulfate cannot be assimilated as the sulfate assimilation pathway is not functional (Parkhill et al ((2003); Nat. Genet. 35:32-40)). Thus the use of high concentrations of cysteine in a medium can provide sulfate ions which, as described above, inhibit virulence factor expression. However Bogdan et al acknowledged that cysteine was required for growth, thus the media disclosed in Bogdan et al (even those containing supposedly reduced amounts of cysteine) contain relatively high concentrations of cysteine. Similarly Jebb and Tomlinson (J. Gen. Microbiol. 17, 59-68) describe the presence of cysteine as being essential for growth. The present inventors, however, have demonstrated for the first time that *Bordetella* can grow in the absence of cysteine and thus that even lower concentrations of cysteine can be used than those disclosed in Bogdan et al.

Cystine is a dimer of cysteine which can be metabolized in a similar way to cysteine by *Bordetella*, but provides twice as much cysteine to the *Bordetella.*

In a further embodiment the chemically defined medium does not comprise cysteine or cystine. In a preferred embodiment the chemically defined medium does not comprise sulfate, cysteine or cystine.

In a further embodiment the chemically defined medium comprises an inorganic source of sulfur selected from the group consisting of thiosulfate, trithionate, tetrathionate, peroxodisulfate, sulphide and sulfite. In a further embodiment the chemically defined medium does not comprise an organic source of sulfur.

The present inventors have demonstrated, for the first time, that inorganic sulfur can be used as a source of sulfur (rather than cysteine) for growing *Bordetella.*

It appears from the art, for example Jebb and Tomlinson (J. Gen. Microbiol. 17, 59-68), that an organic source of sulfur is required for growth of *Bordetella*. This is because it was known that the pathway for synthesis of cysteine from sulfate and thiosulfate does not function in members of the *Bordetella* genus (Parkhill et al ((2003); Nat. Genet. 35:32-40)). However the inventors have demonstrated for the first time that *Bordetella* can grow in the absence of an organic source of sulfur (as long as an inorganic source of sulfur such as thiosulfate is present).

In one embodiment the chemically defined medium comprises thiosulfate. In a further embodiment the chemically defined medium comprises greater than 0.005 mM, greater than 0.006 mM, greater than 0.007 mM, greater than 0.008 mM, greater than 0.010 mM, greater than 0.050 mM, greater than 0.100 mM, between 0.005 mM and 0.100 mM, between 0.005 mM and 0.050 mM, between 0.005 mM and 0.025 mM, around 0.120 mM or around 0.011 mM thiosulfate. In a further embodiment the chemically defined medium comprises trithionate. In a further embodiment the chemically defined medium comprises greater than 0.003 mM, greater than 0.004 mM, greater than 0.005 mM, greater than 0.008 mM, greater than 0.010 mM, greater than 0.020 mM, greater than 0.050 mM, between 0.003 mM and 0.500 mM, between 0.003 mM and 0.100 mM, between 0.005 mM and 0.010 mM, around 0.007 mM or around 0.080 mM trithionate. In one embodiment the chemically defined medium comprises tetrathionate. In a further embodiment the chemically defined medium comprises greater than 0.002 mM, greater than 0.003 mM, greater than 0.004 mM, greater than 0.005 mM, greater than 0.025 mM, greater than 0.050 mM, between 0.002 mM and 1.000 mM, between 0.002 mM and 1.000 mM, between 0.010 mM and 0.100 mM, around 0.060 mM or around 0.0006 mM tetrathionate. In one embodiment the chemically defined medium comprises peroxodisulfate. In a further embodiment the chemically defined medium comprises greater than 0.005 mM, greater than 0.006 mM, greater than 0.007 mM, greater than 0.008 mM, greater than 0.010 mM, greater than 0.050 mM, greater than 0.100 mM, between 0.005 mM and 1.000 mM, between 0.005 mM and 0.200 mM, between 0.005 mM and 0.015 mM, around 0.120 mM or around 0.011 mM peroxodisulfate. In one embodiment the chemically defined medium comprises sulphide. In a further embodiment the chemically defined medium comprises greater than 0.010 mM, greater than 0.012 mM, greater than 0.014 mM, greater than 0.016 mM, greater than 0.020 mM, greater than 0.100 mM, greater than 0.200 mM, between 0.010 mM and 1.000 mM, between 0.010 mM and 0.300 mM, between 0.010 mM and 0.100 mM, around 0.240 mM or around 0.022 mM sulphide. In one embodiment the chemically defined medium comprises sulphite. In a further embodiment the chemically defined medium comprises greater than 0.010 mM, greater than 0.012 mM, greater than 0.014 mM, greater than 0.016 mM, greater than 0.020 mM, greater than 0.100 mM, greater than 0.200 mM, around 0.240 mM or around 0.022 mM sulphite.

In one embodiment the chemically defined medium comprises thiosulfate and trithionate, thiosulfate and tetrathionate, thiosulfate and peroxodisulfate, thiosulfate and sulphide, thiosulfate and sulphite, trithionate and tetrathionate, trithionate and peroxodisulfate, trithionate and sulphide, tritionate and sulphite, tetrathionate and peroxodisulfate, tetrathionate and sulphide, tetathionate and sulphite, peroxodisulfate and sulphide, peroxodisulfate and sulphite or sulphide and sulphite. In a further embodiment the chemically defined medium comprises, 2, 3, 4, 5, 6 or more of the inorganic sources of sulfur selected from the group consisting of thiosulfate, trithionate, tetrathionate, peroxodisulfate, sulphide and sulphite.

In a preferred embodiment the chemically defined medium does not comprise sulfate, cysteine or cystine and does comprise greater than 0.005 mM, greater than 0.006 mM, greater than 0.007 mM, greater than 0.008 mM, greater than 0.010 mM, greater than 0.050 mM, greater than 0.100 mM, between 0.005 mM and 0.100 mM, between 0.005 mM and 0.050 mM, between 0.005 mM and 0.025 mM, around 0.120 mM or around 0.011 mM thiosulfate.

Buffer

In a further embodiment the chemically defined medium comprises a buffer selected from the group consisting of MOPS, MES, HEPES and PIPES.

The present inventors have surprisingly found that a chemically defined medium comprising buffers other than tris and β-glycerophosphate, in particular MOPS buffer demonstrates improved growth rates for *Bordetella pertussis* compared with other media. Alternative buffers for use in chemically defined media for *Bordetella pertussis* were explored by Lothe et al (Journal of Biological Standardisation (1985) 13, 129-134), however they concluded that β glycerophosphate was the superior buffer. The present inventors have found, however, not only that further buffers may be effective, but also that MOPS demonstrates improvements over β-glycerophosphate. For this reason the present inventions provides a chemically defined medium comprising a MOPS buffer. In one embodiment the buffer is MOPS at a concentration of greater than 2 mM, greater than 5 mM, greater than 7 mM, greater than 9 mM, greater than 10 mM, greater than 11 mM, between 2 mM and 100 mM, between 2 mM and 50 mM, between 5 mM and 20 mM or around 12 mM.

High Concentrations of Copper

It was demonstrated that copper was not required in a medium for *Bordetella* (Stainer and Scholte Journal of General Microbiology (1971), 63:211-220), however the present inventors have surprisingly found that adding a relatively high concentration of copper to a chemically defined medium for *Bordetella* leads to a significant increase in the amount of toxin produced by the *Bordetella* (for example the expression of Pertussis Toxin from *Bordetella pertussis*).

Thus in a further embodiment the chemically defined medium comprises greater than 2 μM, greater than 3 μM, greater than 4 μM, greater than 5 μm, greater than 6 μM, greater than 7 μM, greater than 8 μM, less than 200 μM, less than 150 μM, less than 100 μM, between 4 μM and 10 μM, between 2 μM and 200 μM, between 3μM and 150 μM,or between 5 μM and 100 μM copper. In an embodiment the source of the copper is selected from the group consisting of copper chloride, copper sulfate, copper acetate, copper chlorate and copper carbonate. In a further embodiment the copper is in the form of copper chloride.

High Concentrations of Magnesium

Higher concentrations of magnesium have been known to modulate *Bordetella*, and to induce conversion of *Bordetella* to a state where they are less likely to express virulence factors such as Pertussis Toxin and FHA (Idigbe et al J. MED. MICROBIOL (1981) 409-418) and Lacey et al ((1960) J. Hyg. 58:57-93)). As explained above, growing

*Bordetella* in an environment which induces high levels of toxin expression is advantageous, addition of magnesium was known to reduce virulence factor expression and thus removed from media for *Bordetella* vaccine production. However the present inventors have surprisingly found that the addition of high concentrations of magnesium can be used in a chemically defined medium with high levels of expression of virulence factors such as PT.

For these reasons in one embodiment the chemically defined medium comprises greater than 2 μM, greater than 5 μM, greater than 10 μM, greater than 25 μM, greater than 50 μM, greater than 75 μM, greater than 100μM, greater than 200 μM, greater than 300 μM, greater than 400 μM, between 2 μM and 6000 μM, between 1000 μM and 6000 μM or around 5000 μM magnesium.

Amino Acid Source

It is generally known that media must include a nitrogen source and a carbon source; in many cases certain amino acids are required for growth (essential amino acids). Stainer and Scholte (Stainer and Scholte Journal of General Microbiology (1971), 63:211-220) attempted to create a simplified chemically defined medium, however they concluded that at least two amino acids were required, namely glutamic acid, proline and cystine.

However the present inventors have surprisingly found *Bordetella* can grow in media comprising only a single type of amino acid. In particular the inventors have demonstrated that *Bordetella* can grow on media which comprises only a single amino acid and does not comprise cysteine, this is particularly surprising as, as described above, it was previously thought that cysteine was required as a source of Sulfur. This is advantageous because, as described above, media for commercial use should be as simple as possible in order to reduce difficulties in manufacture of the medium, cost of the medium and potential sources of variability from batch to batch.

For this reason, in one embodiment, the chemically defined medium comprises a sole amino acid source. The term ‘sole amino acid source’ refers to a compound which provides the medium with a source of one type of amino acid (such as a source of glutamine, or asparagine or another amino acid), a compound such as cystine can be considered a sole amino acid source since although this is a dipeptide, this only contains cysteine and thus only a single amino acid is supplied. Noteably a medium will be considered to comprise a sole amino acid source if both cysteine and cystine are present, since both of these compounds supply only cysteine (the sole amino acid) to the medium. This term includes D- and L-enantiomers of the amino acids. In one embodiment the amino acid source is a D-enantiomer, in a further embodiment the amino acid source is an L-enantiomer, in a further embodiment the amino acid source may be either an L-enantiomer or a D-enantiomer. A medium with a ‘sole amino acid source’ does not comprise other amino acids, for example, a medium with cysteine as the sole amino acid source does not comprise glutamate, alanine, aspartate, phenylalanine, glycine, histidine, isoleucine, lysine, leucine, methionine, asparagine, proline, glutamine, serine, valine, tyrosine or any other amino acids. As explained above the term ‘does not comprise’ a certain substrate such as certain amino acids refers to a medium in which the creator of the medium has not added a significant amount of that substance. Thus a medium can be considered to ‘not comprise’ a certain substance if the medium comprises a small amount of that substance, which is for instance, a contaminant. Alternatively a medium can be considered to ‘not comprise’ a certain substance if the creator of the medium has added a very small amount of that substance which is not sufficient to alter the yield of a virulence factor such as Pertussis Toxin. This can be determined by culturing the species of *Bordetella* in the presence of the small amount of that substance and in the absence of the small amount of that substance and measure the yield of that virulence factor in these two cultures using an ELISA (as described above). In a further embodiment the sole amino acid source is a sole nitrogen source.

In an embodiment the sole amino acid source is selected from the group consisting of cysteine, cystine, alanine, glycine, glutamate, proline, serine, glutamine, aspartate, leucine, isoleucine, valine, tyrosine, phenylalanine, tryptophane, histidine, arginine, ornithine, lysine, threonine, asparagine and methionine. In one embodiment the sole amino acid source is cysteine at a concentration of greater than 75 mM, greater than 100 mM, greater than 125 mM, between 75 mM and 250 mM, between 100 mM and 150 mM or around 125 mM. In one embodiment the sole amino acid source is proline at a concentration of greater than 75 mM, greater than 100 mM, greater than 125 mM, between 75 mM and 250 mM, between 100 mM and 150 mM or around 125 mM. In one embodiment the sole amino acid source is glutamate at a concentration of greater than 75 mM, greater than 100 mM, greater than 125 mM, between 75 mM and 250 mM, between 100 mM and 150 mM or around 125 mM. In one embodiment the sole amino acid source is glutamine at a concentration of greater than 75 mM, greater than 100 mM, greater than 125 mM, between 75 mM and 250 mM, between 100 mM and 150 mM or around 125 mM. In one embodiment the sole amino acid source is aspartate at a concentration of greater 10 mM, greater than 20 mM, greater than 30 mM, between 10 mM and 100 mM, between 20 mM and 50 mM or around 30 mM. In one embodiment the sole amino acid source is asparagine at a concentration of greater than 75 mM, greater than 100 mM, greater than 125 mM between 75 mM and 250 mM, between 100 mM and 150 mM or around 125 mM. In one embodiment the sole amino acid source is serine at a concentration of greater than 75 mM, greater than 100 mM, greater than 125 mM between 75 mM and 250 mM, between 100 mM and 150 mM or around 125 mM. In one embodiment the sole amino acid source is alanine at a concentration of greater than 75 mM, greater than 100 mM, greater than 125 mM, between 75 mM and 250 mM, between 100 mM and 150 mM or around 125 mM.

The inventors have further demonstrated that, although it can be advantageous to use a sole amino acid source in a chemically defined medium for *Bordetella* as this can support high production of toxins, it is also possible to develop a medium which does not comprise a source of amino acids at all. This provides for a medium in which carbon and nitrogen sources are provided through separate components, this allows one to manipulate the carbon and nitrogen sources separately. Indeed, Thalen et al. (Journal of Biotechnology (1999) 75: 147-159) reported that a nitrogen to carbon ratio of 1:5 (as found in the medium of Stainer and Scholte (Journal of General Microbiology (1971), 63:211-220)) is not optimal for growth of *Bordetella*, and results in the accumulation of ammonia. Thalen et al. showed that ammonia accumulation could be drastically reduced by using a nitrogen to carbon ratio of 1:10. However, such a ratio cannot be attained with naturally occurring amino acids, for which this ratio is determined by the molecular composition, and ranges from 1:1.5 (Arginine) to 1:9 (Tyrosine and Phenylalanine). To circumvent this limitation, Thalen et al. manipulated the carbon to nitrogen ratio by adding a second source of carbon containing no nitrogen (lactate, an organic acid). However, this solution is complex in terms of metabolic fluxes, which in turn complicates process monitoring and understanding, as well as the achievement of a balanced medium (Neeleman et al. (Applied Microbiology and Biotechnology (2001), 57:489-493)). Completely avoiding amino acids offers an alternative solution to precisely manipulate the carbon to nitrogen ratio, by carefully adjusting the relative concentrations of a carbon source containing no nitrogen, on one hand, and a nitrogen source containing no carbon, on the other hand. For this reason in a further embodiment the chemically defined medium does not comprise a source of amino acids.

The medium should contain a source of carbon, if the medium does not contain an amino acid source the source of carbon is preferably an organic acid. In one embodiment the organic acid is selected from the group consisting of citrate lactate, actetate, pyruvate, fumarate and succinate. The present inventors have demonstrated that organic acids are suitable replacements for glutamate as a carbon source for *Bordetella* supporting reasonable levels of growth.

In one embodiment, if the chemically defined medium comprises a single amino acid source, or does not comprise a source of amino acids, the chemically defined medium further comprises at least one of the chemically defined medium components comprising potassium hydrogen phosphate, potassium chloride, magnesium, calcium, Fe(III) citrate, MOPS buffer, niacin, dimethyl-β-cyclodextrin, copper, or cobalt, preferably the medium comprises 2, 3, 4, 5, 6, 7, 8, or 9 of these components. In a preferred embodiment the chemically defined medium comprises all of these components. In a further embodiment the chemically defined medium may also comprise sodium, zinc, biotin, riboflavin, calcium pantothenate. Preferably the medium comprises sodium, zinc, biotin, riboflavin and calcium panthothenate.

In a further embodiment the chemically defined medium comprises a single amino acid source or does not comprise a source of amino acids, and the chemically defined medium does comprise between 250 mg/L and 750 mg/L $KH_2PO_4$, between 100 and 300 mg/L KCl, between 500 and 1500 mg/L $MgCl_2.6H_2O$, between 50 mg/L and 150 mg/L $CaCl_2.2H_2O$, between 10 mg/L and 30 mg/L Fe (III)-citrate.$3H_2O$, between 1000 mg/L and 5000 mg/L MOPS, between 4 mg/L and 8 mg/L niacin, between 500 mg/L and 2000 mg/L dimethyl-β-cyclodextrin, between 0.5 mg/L and 2 mg/L $CuCl_2.2H_2O$ and, between 0.1 mg/L and 1 mg/L $CoCl_2.H_2O$. In a further embodiment the medium further comprises between 1 mg/L and 25 mg/L $ZnCl_2$, between 0.01 and 1.00 mg/L biotin, between 0.01 and 1.00 mg/L riboflavin, between 1 mg/L and 10 mg/L calcium pantothenate and between 5000 mg/L and 1500 mg/L NaCl.

Additional Beneficial Additives

As described above, it is considered that a chemically defined medium must contain at least a source of carbon, a source of nitrogen, a source of phosphorus a source of sulfur and a buffer. In general it is advantageous to design a chemically defined medium to be simple (not to contain too many components) as this reduces cost and manufacturing complexity. However the present inventors have demonstrated that addition of an additive selected from the group consisting of zinc, cobalt, thiamine, riboflavin, pantothenate, greater than 0.4 µM biotin, greater than 50 µM calcium, greater than 15 µM niacin, and greater than 25 µM ascorbic acid can significantly improve the yield of expression of virulence factors such as Pertussis Toxin.

For this reason, in one embodiment the chemically defined medium comprises an additive selected from the group consisting of zinc, cobalt, thiamine, riboflavin and pantothenate. In a further embodiment the chemically defined medium comprises an additive selected from the group consisting of greater than 0.4 µM biotin, greater than 50 µM calcium, greater than 15 µM niacin, and greater than 25 µM Ascorbic Acid.

In one embodiment the chemically defined medium comprises at least 2, 3, 4, 5, 6, 7, 8, or 9 of these additives. In a preferred embodiment the chemically defined medium comprises all of zinc, cobalt, riboflavin, thiamine, pantothenate, greater than 0.4 µM biotin, greater than 0.05 mM calcium, greater than 15 µM niacin and greater than 25 µM Ascorbic acid. In an embodiment the concentration of the additive in the chemically defined medium is sufficient for the additive to increase the level of production of virulence factors by the *Bordetella* (this can be examined using the ELISA as described in Example 1 (Determination of PT concentration) for measuring whether addition of an additive alters the yield of pertussis toxin).

In one embodiment the chemically defined medium comprises greater than 0.1 µM, greater than 1 µM, greater than 5 µM, greater than 10 µM, greater than 20 µM, greater than 30 µM, greater than 40 µM, greater than 50 µM, greater than 60 µM, greater than 70 µM, greater than 100 µM, greater than 200 µM, greater than 400 µM, greater than 400 µM, greater than 600 µM, greater than 700 µM, between 10 µM and 2000 µM, between 20 µM and 1000 µM, between 30 µM and 100 µM or around 75 µM zinc. In one embodiment the chemically defined medium comprises greater than 0.05 µM, greater than 0.10 µM, greater than 0.1 5µM, between 0.10 µM and 0.30 µM, between 0.10 µM and 0.20 µM or around 0.18 µM cobalt. In one embodiment the chemically defined medium comprises greater than 0.05 µM, greater than 0.10 µM, greater than 0.15 µM, between 0.05 µM and 5.00 µM, between 0.10 µM and 1.00 µM, or between 0.15 µM and 0.50 µM thiamine. In one embodiment the chemically defined medium comprises greater than greater than 0.1 µM, greater than 0. 2µM, greater than 0.3 µM, greater than 0.4 µM greater than 0.5 µM, greater than 0.6 µM, greater than 0.8 µM, between 0.1 µM and 10 µM, between 0.5 µM and 1.0 µM or around 0.8 µM riboflavin. In one embodiment the chemically defined medium comprises greater than 0.10 µM, greater than 0.5 µM, greater than 1.0 µM, greater than 1.5 µM, greater than 2.0 µM, greater than 5.0 µM, greater than 8.0 µM, between 0.5 µM and 100 µM, between 0.5 µM and 25.0 µM, between 5.0 µM and 10.0 µM, or around 8.0 µM pantothenate. In one embodiment the chemically defined medium comprises greater than 0.4 µM greater than 0.5 µM, greater than 0.6 µM, greater than 0.8 µM, between 0.5 µM and 100 µM, between 0.5 µM and 25.0 µM, between 5.0 µM and 10.0 µM, or around 8.0 µM biotin. In one embodiment the chemically defined medium comprises greater than 100 µM, greater than 120 µM, greater than 140 µM, between 50 µM and 1000 µM, between 50 µM and 500 µM, between 100 µM and 200 µM or around 140 µM calcium. In one embodiment the chemically defined medium comprises greater than 20 µM, greater than 30 µM, greater than 35 µM, between 15 µM and 500 µM, between 15 µM and 100 µM, between 25 µM and 75 µM or around 50 µniacin. In one embodiment the chemically defined medium comprises greater than 50 µM, greater than 75 µM, greater than 100 µM, greater than 1000 µM, greater than 2000 µM, greater than 3000 µM, between 25 µM and 10000 µM, between 10000 µM and 5000 µM, or around 3500 µM Ascorbic Acid.

In a preferred embodiment the chemically defined medium comprises greater than 0.01 mM zinc, greater than 0.0005 mM cobalt, greater than 0.005 mM thiamine, greater than 0.0001 mM riboflavin, greater than 0.005 pantothenate, greater than 0.4 μM biotin, greater than 0.05 mM calcium, greater than 15 μM niacin and greater than 25 μM Ascorbic Acid.

In a further preferred embodiment the chemically defined medium comprises greater than 700 μM zinc, greater than 0.15 μM cobalt, greater than 29 μM thiamine, greater than 0.8 μM riboflavin, greater than 8.0 μM pantothenate, greater than 0.8 μM biotin greater than 140 μM calcium, greater than 35 μM niacin, and greater than 3000 μM Ascorbic Acid.

In a further preferred embodiment the chemically defined medium comprises between 10 μM and 150 μM zinc, between 0.10 μM and 0.30 μM cobalt, between 25 μM and 200 μM thiamine, between 0.1 μM and 10 μM riboflavin, between 0.5 μM and 100 μM pantothenate, between 0.5 μM and 100 μM biotin, between 50 μM and 1000 μM calcium, between 1 μM and 500 μM niacin and between 25 μM and 10000 μM Ascorbic Acid.

In a further preferred embodiment the chemically defined medium comprises between 30 μM and 80 μM zinc, between 0.10 μM and 0.20 μM cobalt, between 25 μM and 50 μM thiamine, between 0.5 μM and 1.0 μM riboflavin, between 5.0 μM and 10.0 μM pantothenate, between 5.0 μM and 10.0 μM biotin, between 100 μM and 200 μM calcium, between 25 μM and 75 μM niacin, and between 10000 μM and 5000 μM Ascorbic Acid.

Amino Acid Concentrations

The present inventors have further demonstrated that prior art media such as Stainer Scholte can be improved by addition of high levels of aspartate, glycine, methionine and leucine. Thus in a further embodiment there is provided a chemically defined medium which comprises an amino acid sequence from the group consisting of aspartate at a concentration greater than 1000 μM, glycine at a concentration of greater than 1000 μM methionine at a concentration of greater than 500 μM and leucine at a concentration of greater than 1500 μM.

In one embodiment the chemically defined medium comprises aspartate at a concentration of greater than 1000 μM, greater than 2000 μM, greater than 2450 μM, greater than 3000 μM, greater than 3500 μM, between 1000 μM and 10000 μM, between 1000 μM and 5000 μM or around 4000 μM. In a further embodiment the chemically defined medium comprises glycine at a concentration of greater than 500 μM, greater than 1000 μM, greater than 1500 μM, greater than 1750 μM, between 500 μM and 5000 μM, between 500 μM and 2500 μM or around 2000 μM. In a further embodiment the chemically defined medium comprises methionine at a concentration of greater than 100 μM, greater than 300 μM, greater than 500 μM, greater than 600 μM, greater than 700 μM, between 100 μM and 2000 μM, between 100 μM and 1000 μM or around 775 μM. In a further embodiment the chemically defined medium comprises leucine at a concentration of greater than 500 μM, greater than 1000 μM, greater than 1500 μM, greater than 2000 μM, greater than 2500 μM, greater than 3000 μmM, between 500 μM and 10000 μM, between 500 μM and 5000 μM, between 3000 μM and 4000 μM or around 3300 μM. In one embodiment the chemically defined medium comprises at least 2, 3 or 4 of aspartate at a concentration greater than 100 μM, glycine at a concentration of greater than 1000 μM, methionine at a concentration of greater than 500 μm and leucine at a concentration of greater than 1500 μm. In a preferred embodiment the chemically defined medium of the invention comprises aspartate at a concentration greater than 1000 μM, glycine at a concentration of greater than 1000 μM, methionine at a concentration of greater than 500 μM and leucine at a concentration of greater than 1500 μM.

In a further embodiment the chemically defined medium comprises glutamate at a concentration of greater than 50 mM, greater than 75 mM, greater than 90 mM, greater than 100 mM, greater than 110 mM, between 50 mM and 500 mM, between 50 mM and 250 mM, between 100 mM and 150 mM or around 120 mM. In a further embodiment the chemically defined medium comprises alanine at a concentration of greater than 1000 μM, greater than 1500 μM, greater than 2000 μM, greater than 2500 μM, greater than 3000 μM, between 1000 μM and 10000 μM, between 1000 μM and 5000 μM, between 3000 μM and 4000 μM or around 3400 μM. In a further embodiment the chemically defined medium comprises phenylalanine at a concentration of greater than 500 μM, greater than 750 μM, greater than 1000 μM, greater than 1250 μM, greater than 1400 μM, between 500 μM and 10000 μM, between 500 μM and 5000 μM, between 1000 μM and 2000 μM or around 1400 μM. In a further embodiment the chemically defined medium comprises histidine at a concentration of greater than 50 μM, greater than100 μM, greater than 150 μM, greater than 200 μM, between 50 μM and 1000 μM, between 50 μM and 500 μM, between 150 μM and 250 μM or around 200 μM. In a further embodiment the chemically defined medium comprises isoleucine at a concentration of greater than 500 μM, greater than 1000 μM, greater than 1500 μM, greater than 1750 μM, between 500 μM and 5000 μM, between 500 μM and 2500 μM, between 1000 μM and 2000 μM or around 1800 μM. In a further embodiment the chemically defined medium comprises lysine at a concentration of greater than 500 μM, greater than 1000 μM, greater than 1500 μM, greater than 2000 μM, between 500 μM and 10000 μM, between 500 μM and 5000 μM, between 1500 μM and 2500 μM or around 2100 μM. In a further embodiment the chemically defined medium comprises proline at a concentration of greater than 1000 μM, greater than 3000 μM, greater than 4000 μM, greater than 5000 μM, greater than 6000 μM, greater than 7000 μM, between 1000 μM and 50000 μM, between 1000 μM and 10000 μM, between 7000 μM and 8000 μM or around 7600 μM. In a further embodiment the chemically defined medium comprises serine at a concentration of greater than 500 μM, greater than 1000 μM, greater than 1500 μM, greater than 1700 μM, between 500 μM and 10000 μM, between 500 μM and 5000 μM, between 1000 μM and 2000 μM or around 1700 μM. In a further embodiment the chemically defined medium comprises valine at a concentration of greater than 1000 μM, greater than 2000 μM, greater than 2500 μM, greater than 3000 μM, between 1000 μM and 10000 μM, between 1000 μM and 5000 μM, between 3000 μM and 4000 μM or around 3400 μM. In a further embodiment the chemically defined medium comprises tyrosine at a concentration of greater than 25 μM, greater than 50 μM, greater than 75 μM, greater than 100 μM, greater than 150 μM, greater than 175 μM, between 25 μM and 1000 μM, between 25 μM and 500 μM, between 100 μM and 200 μM or around 180 μM. In a further embodiment the chemically defined medium comprises glutathione at a concentration of greater than 100 μM, greater than 200 μM, greater than 400 μM, greater than 500 μM. greater than 600 μM, greater than 700 μM, between 100 μM and 5000 μM, between 100 μM and 2500 μM, between 100 μM and 1000 μM or around 750 μM. In a preferred embodiment the chemically defined medium comprises glutamate at a concentration of greater than 50 mM, alanine at a concentration of greater than 1000 μM, aspartate at a concentration of greater than 1000 μM, phenylalanine at a concentration of greater than 500 μM, glycine at a concentration of greater than 500 μM, histidine at a concentration of greater than 50 μM, isoleucine at a concentration of greater than 500 μM, lysine at a concentration of greater than 500 μM, leucine at a concentration of greater than 500 μM, methionine at a concentration of greater than 100 μM, proline at a concentration of greater than 1000 μM, serine at a concentration of greater than 500 μM, valine at a concentration of greater than 1000 μM, tyrosine at a concentration of greater than 25 μM and glutathione at a concentration of greater 700 μM. In a further preferred embodiment the chemically defined medium comprises glutamate at a concentration of greater than 110 mM, alanine at a concentration of greater than 3000 μM, aspartate at a concentration of greater than 3500 μM, phenylalanine at a concentration of greater than 1400 μM, glycine at a concentration of greater than 1750 μM. histidine at a concentration of greater than 200 μM, isoleucine at a concentration of greater than 1750 μM, lysine at a concentration of greater than 2000 μM, leucine at a concentration of greater than 3000 μM, methionine at a concentration of greater than 700 μM, proline at a concentration of greater than 7000 μM, serine at a concentration of greater than 1700 μM, valine at a concentration of greater than 3000 μM, tyrosine at a concentration of greater than 175 μM and glutathione at a concentration of greater than 700 μM.

In a preferred embodiment the chemically defined medium comprises aspartate at a concentration of between 1000 μM and 10000 μM, glycine at a concentration of between 500 μM and 5000 μM, methionine at a concentration of between 100 μM and 2000 μM, leucine at a concentration of between 500 μM and 10000 μM, glutamate at a concentration of between 50 mM and 500 mM, alanine at a concentration of between 1000 μM and 10000 μM, phenylalanine at a concentration of between 500 μM and 10000 μM, histidine at a concentration of between 50 μM and 1000 μM, isoleucine at a concentration of between 500 μM and 5000 μM, lysine at a concentration of between 500 μM and 10000 μM, proline at a concentration of between 1000 μM and 50000 μM, serine at a concentration of between 500 μM and 10000 μM, valine at a concentration of between 1000 μM and 10000 μM, tyrosine at a concentration of between 25 μM and 1000 μM and glutathione at a concentration of between 100 μM and 5000 μM.

In a preferred embodiment the chemically defined medium comprises aspartate at a concentration of between 1000 μM and 5000 μM, glycine at a concentration of between 500 μM and 2500 μM, methionine at a concentration of between 100 μM and 1000 μM, leucine at a concentration of between 3000 μM and 4000 μM, glutamate at a concentration of between 100 mM and 150 mM, alanine at a concentration of between 3000 μM and 4000 μM, phenylalanine at a concentration of between 1000 μM and 2000 μM, histidine at a concentration of between 150 μM and 250 μM, isoleucine at a concentration of between 1000 μM and 2000 μM, lysine at a concentration of between 1500 μM and 2500 μM, proline at a concentration of between 7000 μM and 8000 μM, serine at a concentration of between 1000 μM and 2000 μM, valine at a concentration of between 3000 μM and 4000 μM, tyrosine at a concentration of between 100 μM and 200 μM and glutathione at a concentration of between 100 μM and 1000 μM.

Ratios of Components

The present inventors have surprisingly found that if certain ratios of compounds are used the chemically defined medium will provide improved yields of virulence factors such as Pertussis Toxin and FHA. For this reason there is provided a chemically defined medium that comprises at least two components and wherein the at least two components are selected from the group consisting of:

(a) carbon and phosphorus at a ratio of greater than 100:1, greater than 125:1, greater than 150:1, greater than 175:1 or greater than 200:1 (carbon:phosphorus) (mol/mol);

(b) glutamate and phosphorus at a ratio of greater than 20:1, greater than 22:1, greater than 24:1 or greater than 25:1 (glutamate:phosphorus) (mol/mol);

(c) carbon and magnesium at a ratio of less than 600:1, less than 500:1, less than 400:1 or less than 300:1 (carbon: magnesium) (mol/mol);

(d) glutamate and magnesium at a ratio of less than 115:1, less than 110:1, less than 105:1 or less than 100:1 (glutamate:magnesium) (mol/mol);

(e) carbon and copper at a ratio of greater than 3000:1, greater than 3500:1, or greater than 4000:1 (carbon: copper) (mol/mol);

(f) glutamate and copper at a ratio of greater than 170:1, greater than 180:1, greater than 200:1 or greater than 250:1 (glutamate:copper) (mol/mol);

(g) carbon and iron at a ratio of greater than 9500:1, greater than 1000:1, greater than 1250:1 or greater than 1500:1 (carbon:iron) (mol/mol);

(h) glutamate and iron at ratio of greater than 1600:1, greater than 1800:1, greater than 2000:1 or greater than 2500:1 (glutamate:iron) (mol/mol);

(i) carbon and glycine at a ratio of less than 500:1, less than 400:1, less than 300:1 or less than 250:1 (carbon:glycine) (mol/mol);

(j) glutamate and glycine at a ratio of less than 100:1, less than 80:1, less than 75:1 or less than 60:1 (glutamate: glycine) (mol/mol);

(k) carbon and leucine at a ratio of less than 440:1, less than 400:1, less than 350:1 or less than 300:1 (carbon:leucine) (mol/mol);

(l) glutamate and leucine at a ratio of less than 75:1, less than 70:1, less than 60:1 or less than 50:1 (glutamate: leucine) (mol/mol);

(m) carbon and methionine at a ratio of less than 1200:1, less than 1000:1, less than 800:1 or less than 750:1 (carbon: methionine) (mol/mol);

(n) glutamate and methionine at a ratio of less than 200:1, less than 175:1, less than 150:1 or less than 120:1 (glutamate:methionine) (mol/mol);

(o) carbon and calcium at a ratio of greater than 3750:1, greater than 4000:1, greater than 4500:1 or greater than 5000:1 (carbon:calcium) (mol/mol);

(p) glutamate and calcium at a ratio of greater than 620:1, greater than 650:1, greater than 675:1 or greater than 750:1 (glutamate:calcium) (mol/mol);

(q) carbon and cobalt at a ratio of greater than 3000:1, greater than 3500:1, greater than 4750:1 or greater than 5000:1 (carbon:cobalt) (mol/mol);

(r) glutamate and cobalt at a ratio of greater than 750:1, greater than 1000:1, greater than 1250:1 or greater than 1500:1 (glutamate:cobalt) (mol/mol);

(s) carbon and zinc at a ratio of greater than 3000:1, greater than 3500:1, greater than 4000:1 or greater than 5000:1 (carbon:zinc) (mol/mol);

(t) glutamate and zinc at a ratio of greater than 750:1, greater than 1000:1, greater than 1250:1 or greater than 1500:1 (glutamate:zinc) (mol/mol);

(u) carbon and sulfate equivalents at a ratio of greater than 750:1, greater than 1000:1, greater than 1250:1 or greater than 1500:1 (carbon:sulfate equivalents) (mol/mol); and (v) glutamate and sulfate equivalents at a ratio of greater than 130:1, greater than 150:1, greater than 175:1 or greater than 200:1 (glutamate:sulfate equivalents) (mol/mol).

In one embodiment the chemically defined medium comprises at least 2, 3, 4, 5, 6, 7, 8, 9, 10, 11, 12, 13, 14, 15, 16, 17, 18, 19, 20, 21 or all 22 of (a), (b), (c), (d), (e), (f), (g), (h), (i), (j), (k), (l), (m), (n), (o), (p), (q), (r), (s), (t), (u) and (v). In one embodiment the chemically defined medium comprises carbon and phosphorus at a ratio of greater than 200:1 (carbon:phosphorus) (mol/mol), glutamate and phosphorus at a ratio of greater than 25:1 (glutamate: phosphorus) (mol/mol), carbon and magnesium at a ratio of less than 300:1 (carbon:magnesium) (mol/mol), glutamate and magnesium at a ratio of less than 100:1 (glutamate:magnesium) (mol/mol), carbon and copper at a ratio of greater than 4000:1 (carbon:copper) (mol/mol), glutamate and copper at a ratio of greater than 250:1 (glutamate:copper) (mol/mol), carbon and iron at a ratio of greater than 1500:1 (carbon: iron) (mol/mol), glutamate and iron at a ratio of greater than 2500:1 (glutamate:iron) (mol/mol), carbon and glycine at a ratio of less than 250:1 (carbon:glycine) (mol/mol), glutamate and glycine at a ratio of less than 250:1 (carbon; glycine) (mol/mol), carbon and leucine at a ratio of less than 300:1 (carbon:leucine) (mol/mol), glutamate and leucine at a ratio of less than 50:1 (glutamate:leucine) (mol/mol), carbon and methionine at a ratio of less than 750:1 (carbon: methionine) (mol/mol), glutamate and methionine at a ratio of less than 120:1 (glutamate:methionine) (mol/mol), carbon and calcium at a ratio of greater than 5000:1 (carbon: calcium) (mol/mol); glutamate and calcium at a ratio of greater than 750:1 (glutamate:calcium) (mol/mol), carbon and cobalt at a ratio of greater than 5000:1 (carbon:cobalt) (mol/mol), glutamate and cobalt at a ratio of greater than 1500:1 (glutamate:cobalt) (mol/mol), carbon and zinc at a ratio of greater than 5000:1 (carbon:zinc), glutamate and zinc at a ratio of greater than 1500:1 (glutamate:zinc) (mol/mol), carbon and sulfate equivalents at a ratio of greater than 1500:1 (carbon:sulfate equivalents) and glutamate and sulfate equivalents at a ratio of greater than 200:1 (glutamate: sulfate equivalents).

The term ‘sulfate equivalents’ refers to inorganic sulfate or organic compounds whose catabolism results in sulfate production (including but not limited to cysteine, cystine and glutathione).

Medium Comprising FE(III)

*Bordetella* media tend to include iron in the form of Fe(II) ions such as Stainer Scholte medium which comprises $FeSO_4$ (Stainer and Scholte Journal of General Microbiology (1971), 63:211-220), however the present inventors have demonstrated that Fe(III) ions may also be used in a medium for *Bordetella*, and further more that a medium comprising Fe(III) ions (such as Fe(III) citrate) provides higher levels of production of virulence factors such as Pertussis Toxin than a medium comprising Fe(II) ions (such as $FeSO_4$).

Thus in one embodiment the chemically defined medium comprises Fe(III) ions. Similarly in one embodiment the chemically defined medium comprises Fe(II) or Fe(III) complexed to an organic compound, preferably the chemically defined medium comprises Fe(III) complexed to an organic compound. In one embodiment the organic compound is an organic compound selected from the group consisting of heme, haemoglobin, myoglobin, transferrin, ferritin, lactoferrin, enterobactin, aerobactin, alcaligin, coprogen, ferrichrome, desferrioxamine, ferroxamine, hydroxamate, citrate and dihydroxybenzoylserine. In one embodiment the chemically defined medium comprises Fe(III) complexed to citrate. In a further embodiment the chemically defined medium comprises greater than 10 μM, greater than 20 μM, greater than 30 μM, greater than 40 μM, greater than 50 μM, between 10 μM and 500 μM, between 10 μM and 100 μM, between 25 μM and 75 μM or around 60 μM Fe(III)citrate.

Further Medium Components

The medium of the invention may comprise further components to those described above. For example the chemically defined medium may comprise chloride. In one embodiment the chemically defined medium comprises chloride at a concentration of less than 45 mM, less than 40 mM, less than 35 mM, less than 30 mM, less than 25 mM, less than 20 mM or less than 15 mM, between 0.1 mM and 500 mM, between 10 mM and 20 mM or around 16 mM chloride. The chemically defined medium may comprise acetate, in one embodiment the chemically defined medium comprises acetate at a concentration of greater than 1 mM, greater than 2 mM, greater than 3 mM greater than 4 mM, between 1 mM and 100 mM, between 4 mM and 6 mM or around 5 mM acetate. The chemically defined medium may comprise potassium. In one embodiment the chemically defined medium comprises potassium at a concentration of greater than 1 mM, greater than 2 mM, greater than 3 mM, greater than 4 mM, greater than 5 mM, greater than 6 mM, between 1 mM and 100 mM, between 5.5 mM and 7 mM or around 6.5 mM. The chemically defined medium may comprise a source of phosphorus, in one embodiment the source of phosphorus comprises phosphate at a concentration of greater than 0.5 mM, greater than 1 mM, greater than 1.5 mM, greater than 2 mM, greater than 2.5 mM, between 0.5 mM and 100 mM, between 3 mM and 4 mM or around 3.6 mM. The chemically defined medium may comprise dimethyl-β-cyclodextrin. In one embodiment the chemically defined medium comprises dimethyl-β-cyclodextrin at a concentration of greater than 0.1 mM, greater than 0.2 mM, greater than 0.3 mM, greater than 0.4 mM, greater than 0.5 mM, greater than 0.6 mM, between 0.01 mM and 10 mM, between 0.7 mM and 0.8 mM or around 0.75 mM.

In one embodiment the chemically defined medium does not comprise sulfate, cysteine or cystine and does comprise greater than 0.008mM thiosulfate, greater than 11 mM MOPS, greater than 6 μM copper, greater than 400 μM Magnesium, greater than 700 μM zinc, greater than 0.15 μM cobalt, greater than 0.15 μM cobalt, greater than 29 μM thiamine, greater than 0.8 μM riboflavin, greater than 8.0 μM pantothenate, greater than 0.8 μM biotin greater than 140 μM calcium, greater than 35 μM niacin, greater than 3000 μM Ascorbic Acid, glutamate at a concentration of greater than 110 mM, alanine at a concentration of greater than 3000 μM, aspartate at a concentration of greater than 3500 μM, phenylalanine at a concentration of greater than 1400 μM, glycine at a concentration of greater than 1750 μM, histidine at a concentration of greater than 200 μM, isoleucine at a concentration of greater than 1750 μM, lysine at a concentration of greater than 2000 μM, leucine at a concentration of greater than 3000 μM, methionine at a concentration of greater than 700 μM, proline at a concentration of greater than 7000 μM, serine at a concentration of greater than 1700 μM, valine at a concentration of greater than 3000 μM, tyrosine at a concentration of greater than 175 μM, glutathione at a concentration of greater than 700 μM, less than 15 mM Chloride, greater than 4 mM acetate, greater than 6 mM potassium, greater than 0.6 mM dimethyl-β-cyclodextrin and greater than 2.5 mM phosphate; optionally the chemically defined medium further comprises sodium and greater than 50 μM Fe(III) citrate.

In one embodiment the chemically defined medium does not comprise sulfate, cysteine or cystine and does comprise between 0.005 mM and 0.100 mM thiosulfate, between 2 mM and 100 mM MOPS, between 2 μM and 200 μM copper, between 2 μM and 6000 μM Magnesium, between 10 μM and 150 μM zinc, between 0.10 μM and 0.30 μM cobalt, between 25 μM and 200 μM thiamine, between 0.1 μM and 10 μM riboflavin, between 0.5 μM and 100 μM pantothenate, between 0.5 μM and 100 μM biotin, between 50 μM and 1000 μM calcium, between 1 μM and 500 μM niacin, between 25 μM and 10000 μM Ascorbic Acid, aspartate at a concentration of between 1000 μM and 10000 μM, glycine at a concentration of between 500 μM and 5000 μM, methionine at a concentration of between 100 μM and 2000 μM, leucine at a concentration of between 500 μM and 10000 μM, glutamate at a concentration of between 50 mM and 500 mM, alanine at a concentration of between 1000 μM and 10000 μM, phenylalanine at a concentration of between 500 μM and 10000 μM, histidine at a concentration of between 50 μM and 1000 μM, isoleucine at a concentration of between 500 μM and 5000 μM, lysine at a concentration of between 500 μM and 10000 μM, proline at a concentration of between 1000 μM and 50000 μM, serine at a concentration of between 500 μM and 10000 μM, valine at a concentration of between 1000 μM and 10000 μM, tyrosine at a concentration of between 25 μM and 1000 μM, glutathione at a concentration of between 100 μM and 5000 μM, between 0.1 mM and 500 mM chloride, between 1 mM and 100 mM acetate, between 1 mM and 100 mM potassium, between 0.01 mM and 10 mM dimethyl-β-cyclodextrin and between 0.5 mM and 100 mM phosphate; optionally the chemically defined medium further comprises sodium and between 10 μM and 500 μM Fe(III citrate).

In one embodiment the chemically defined medium does not comprise sulfate, cysteine or cystine and does comprise between 0.005 mM and 0.025 mM thiosulfate, between 5 mM and 20 mM MOPS, between 4 μM and 10 μM copper, between 1000 μM and 6000 μM, between 30 μM and 80 μM zinc, between 0.10 μM and 0.20 μM cobalt, between 25 μM and 50 μM thiamine, between 0.5 μM and 1.0 μM riboflavin, between 5.0 μM and 10.0 μM pantothenate, between 5.0 μM and 10.0 μM biotin, between 100 μM and 200 μM calcium, between 25 μM and 75 μM niacin, between 10000 μM and 5000 μM Ascorbic Acid, aspartate at a concentration of between 1000 μM and 5000 μM, glycine at a concentration of between 500 μM and 2500 μM, methionine at a concentration of between 100 μM and 1000 μM, leucine at a concentration of between 3000 μM and 4000 μM, glutamate at a concentration of between 100 mM and 150 mM, alanine at a concentration of between 3000 μM and 4000 μM, phenylalanine at a concentration of between 1000 μM and 2000 μM, histidine at a concentration of between 150 μM and 250 μM, isoleucine at a concentration of between 1000 μM and 2000 μM, lysine at a concentration of between 1500 μM and 2500 μM, proline at a concentration of between 7000 μM and 8000 μM, serine at a concentration of between 1000 μM and 2000 μM, valine at a concentration of between 3000 μM and 4000 μM, tyrosine at a concentration of between 100 μM and 200 μM and glutathione at a concentration of between 100 μM and 1000 μM, between 10 mM and 20 mM Chloride, between 4 mM and 6 mM acetate, between 5.5 mM and 7 mM potassium, between 0.7 mM and 0.8 mM dimethyl-β-cyclodextrin and between 3 mM and 4 mM phosphate; the chemically defined medium optionally further comprises sodium and between between 25 μM and 75 μM Fe(III citrate).

Fermentation Process

The invention further provides a fermentation process for growing a species of *Bordetella* in a chemically defined medium (CDM) comprising (a) inoculating the chemically defined medium of the invention with the species of *Bordetella;*

(b) maintaining the species of *Bordetella* in the chemically defined medium for a period of time sufficient to allow biomass accumulation.

The term 'fermentation process' refers to an industrial-scale process for growing cells and/or expressing a virulence factor from those cells. the term 'industrial scale refers to a process in a fermentor, in one embodiment industrial scale process is a process in a fermentor with a working volume of between 5 and 10000 liters, between 10 and 5000 liters, between 20 and 2000 liters, between 50 liters and 1000 liters, greater than or equal to 5 liters, greater than or equal to 10 liters, greater than or equal to 15 liters, greater than or equal to 20 liters, greater than or equal to 25 liters, greater than or equal to 50 liters, greater than or equal to 100 liters, less than or equal to 10000 liters, less than or equal to 5000 liters or less than or equal to 2500 liters. In a further embodiment the 'industrial scale process' is a process suitable for the production of greater than 10 mg/L, greater than 15 mg/L or greater than 20 mg/L pertussis toxin.

In one embodiment the fermentation process has an average generation time less than 15 h, less than 12 h, less than 10 h or less than 9 h. A method for determining the average generation time is decribed in the Detailed Description herein.

In a further embodiment the fermentation process yields greater than 10 mg/L, 15 mg/L or 20 mg/L Pertussis Toxin. A method for determining Pertussis Toxin yields is described in the Detailed Description herein.

In one embodiment the fermentation process is carried out at a temperature greater than or equal to 32° C., greater than or equal to 33° C., greater than or equal to 34° C., less than or equal to 45° C., less than or equal to 42° C., less than or equal to 40° C., less than or equal to 38° C., between 32° C. and 45° C., between 33° C. and 42° C., between 33° C. and 40° C. or between 33° C. and 38° C.

In one embodiment antifoam is used during the fermentation process. In a further embodiment the antifoam is polydimethyl siloxane.

In one embodiment the level of dissolved oxygen is between 1 μM and 160 μM, between 15 μM and 140 μM, between 30 μM and 120 μM, between 45 μM and 110 μM, between 60 μM and 100 μM or around 80 μM.

In one embodiment the pH of the fermentation process is between pH 6.0 and pH 7.5, between pH 6.5 and pH 7.0 or around pH 7.2.

Virulence Factor Expression and Purification

In one embodiment the *Bordetella* species expresses at least one virulence factor comprising Pertussis Toxin (PT), Filamentous Haemagglutinin (FHA), Pertactin (PRN), agglutinogen 2 or agglutinogen 3. In one embodiment the *Bordetella* species expresses PT, in one embodiment the *Bordetella* species expresses FHA, in one embodiment the *Bordetella* species expresses PRN, in one embodiment the *Bordetella* species expresses PT and FHA, in one embodiment the *Bordetella* species expresses PT and PRN, in one embodiment the *Bordetella* species expresses PRN and FHA, in one embodiment the *Bordetella* species expresses PT, PRN and FHA. PT, FHA and PRN are well known in the art.

In one embodiment the process further comprises a step c) of purifying the virulence factor to produce a purified virulence factor. The purified virulence factor can be a purified Pertussis Toxin (PT), Filamentous Haemagglutinin (FHA), Pertactin (PRN), agglutinogen 2 or agglutinogen 3. The purified virulence factor can be altered after purification, for example Pertussis Toxin can be chemically detoxified after purification. See also EP 427462 and WO 91/12020 for the preparation of pertussis antigens. In an embodiment step c) involves cell purification using chromatography. In an embodiment the chromatography technique is affinity chromatography, gel filtration, high pressure liquid chromatography (HPLC) or ion exchange chromatography. Optionally the affinity chromatography uses an affinity tag purification column, an antibody purification column, a lectin affinity column, a prostaglandin purification column or a strepavidin column. Optionally the HPLC uses an ion exchange column, a reverse phase column or a size exclusion column. Optionally the ion exchange column is an anion exchange column or a cation exchange column.

The process can further comprise a step d) of formulating an immunogenic composition comprising the purified virulence factor.

The process can further comprise a step e) of adding at least one further antigen to the immunogenic composition. In one embodiment the at least one further antigen is selected from the group consisting of Pertussis Toxin, Filamentous Haemaglutinin, Pertactin, a Fimbrial Agglutinogen, Diphtheria Toxoid, Tetanus Toxoid, at least one conjugated saccharide antigen from *N. meningitidis, Hepatitis* B surface antigen, Inactivated Polio Virus (IPV) and a conjugated saccharide antigen from *Haemophilus influenzae* b. The at least one conjugated saccharide antigen from *N. meningitidis* can be MenC, MenY, MenA and MenW (e.g. A+C, A+Y, A+W, C+Y, C+W, Y+W, A+C+Y, A+C+W, A+Y+W, C+Y+W, A+C+Y+W); optionally MenC and/or MenY is included optionally all four are included.

Alternatively or in addition to the above meningococcal antigens, the immunogenic composition can comprise one or more pneumococcal capsular oligosaccharide or polysaccharide-carrier protein conjugates.

Typically pneumococcal capsular oligosaccharides or polysaccharides (preferably the latter) represented in the compositions of the invention comprise antigens derived from at least four serotypes of pneumococcus. Preferably the four serotypes comprise 6B, 14, 19F and 23F. More preferably, at least 7 serotypes are comprised in the composition, for example those derived from serotypes 4, 6B, 9V, 14, 18C, 19F, and 23F. More preferably still, at least 11 serotypes are comprised in the composition (11 valent), for example those derived from serotypes 1, 3, 4, 5, 6B, 7F, 9V, 14, 18C, 19F and 23F. In a preferred embodiment of the invention at least 13 of such conjugated pneumococcal antigens are comprised, although further antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

In one embodiment the immunogenic composition comprises a pharmaceutically acceptable excipient. In one embodiment the fermentation process comprises a step f) of adding a pharmaceutically acceptable excipient to the immunogenic composition.

In one embodiment the immunogenic composition comprises an adjuvant such as aluminium phosphate or aluminium hydroxide. In one embodiment the fermentation process comprises a step g) of adding an adjuvant to the immunogenic composition. Methods of adsorbing DTPa and DTPw antigens onto aluminium adjuvants are known in the art. See for example WO 93/24148 and WO 97/00697. Usually components adsorbed onto adjuvant are left for a period of at least 10 minutes at room temperature at an appropriate pH for adsorbing most and preferably all of the antigen before mixing the antigens together in the combination immunogenic compositions of the present invention.

Other components are preferably unadsorbed (such as IPV) or adsorbed specifically onto other adjuvants—Hepatitis B surface antigen (HBsAg) being preferably adsorbed onto aluminium phosphate (as described in WO 93/24148) before mixing with other components.

In a further embodiment there is provided a virulence factor obtainable by the process. In a further embodiment there is provided a virulence factor obtained by the process.

In a further embodiment there is provided an immunogenic composition comprising the virulence factor and a pharmaceutically acceptable excipient. In one embodiment the immunogenic composition comprises at least one further antigen. In one embodiment the at least one further antigen is selected from the group consisting of Pertussis Toxin, Filamentous Haemaglutinin, Pertactin, a Fimbrial Agglutinogen, Diphtheria Toxoid, Tetanus Toxoid, at least one conjugated saccharide antigen from *N. meningitidis, Hepatitis* B surface antigen, Inactivated Polio Virus (IPV) and a conjugated saccharide antigen from *Haemophilus influenzae* b (optionally conjugated to Tetanus Toxoid). The at least one conjugated saccharide antigen from *N. meningitidis* can be MenC, MenY, MenA and MenW (e.g. A+C, A+Y, A+W, C+Y, C+W, Y+W, A+C+Y, A+C+W, A+Y+W, C+Y+W, A+C+Y+W); optionally MenC and/or MenY is included optionally all four are included. In one embodiment the vaccine comprises diphtheria toxoid, tetanus toxoid, and at least one of PT, FHA and PRN (a DTPa vaccine).

In one embodiment there is a provided a vaccine comprising the immunogenic composition.

Vaccine preparation is generally described in Vaccine Design—The Subunit and adjuvant approach Ed Powell and Newman; Pellum Press. Advantageously the combination vaccine according to the invention is a paediatric vaccine.

The amount of polysaccharide or oligosaccharide conjugate antigen in each vaccine dose is selected as an amount which induces an immunoprotective response without significant, adverse side effects in typical vaccinees. Such amount will vary depending on which specific immunogens are employed. Generally it is expected that each dose will comprise 1-1000 μg of conjugated polysaccharide or oligosaccharide (expressed in amount of saccharide), preferably 2-100 μg, more preferably 4-40, 2-15, or 3-10 μg, most preferably around or exactly 5 μg.

The content of protein antigens in the vaccine will typically be in the range 1-100μg, preferably 5-50 μg, most typically in the range 5-25 μg.

A suitable amount of antigen for a particular vaccine can be ascertained by standard studies involving observation of antibody titres and other responses in subjects. Following an initial vaccination, subjects can receive one or two booster injections at about 4 weeks intervals or longer.

The vaccine preparations of the present invention can be used to protect or treat a mammal (preferably human) susceptible to infection, by means of administering said vaccine via systemic or mucosal route. These administrations can include injection via the intramuscular, intraperitoneal, intradermal or subcutaneous routes.

In a further aspect there is provided the immunogenic composition or the vaccine as previously described for use in the prevention or treatment of disease.

In a further aspect there is provided the immunogenic composition or the vaccine as previously described for use in the prevention or treatment of *Bordetella pertussis* disease.

In a further aspect there is provided a use of the immunogenic composition or the vaccine as previously described in the prevention or treatment of disease.

In a further aspect there is provided a use of the immunogenic composition or the vaccine as previously described in the preparation of a medicament for the treatment or prevention of bacterial disease.

In a further aspect there is provided a method of preventing or treating disease comprising administering the immunogenic composition or the vaccine as previously described to a patient.

In one embodiment the disease is *Bordetella pertussis* disease.

The term 'Pertussis Toxin' refers to Pertussis Toxin or alternatively to a genetically toxoided form of Pertussis Toxin. In one embodiment the Pertussis Toxin is not a genetic toxoid of Pertussis Toxin.

The term 'comprising' comprise' and 'comprises' can be replaced in all instances with the terms 'consisting', 'consist' and 'consists'. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The term 'consists' means contains to the exclusion of other compounds, composition, steps or groups etcetera.

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

EXAMPLE 1

20L-scale Fermentation of *Bordetella pertussis* in Basic Chemically Defined Media A chemically defined medium (B-CDM) was designed, which was based on the composition of the medium of Stainer & Scholte (SS; Stainer and Scholte, J. Gen. Microbiol. 63:211-220 (1971)), and contained amino acid supplements as well as dimethyl-β-cyclodextrin. Table 1 compares the composition of the original medium of Stainer & Scholte (SS), a modified version of the SS medium containing dimethyl-β-cyclodextrin—a documented growth stimulant of *B. pertussis* (Imaizumi et al., J. Clin. Microbiol. 17:781-786 (1983))—and other minor changes (SS-cyclo), and the basic chemically defined medium (B-CDM).

The SS-cyclo and B-CDM media were evaluated in fermentations COQ467 and COQ365, respectively. For both fermentations, a first shake-flask pre-culture containing 7.5 ml fresh medium (B-CDM) was inoculated with $10^9$ *B. pertussis* CFUs and incubated at 35° C. (+/−1° C.) and 150 rpm for 24 h (+/−1 h). The first pre-culture was used to inoculate a second shake-flask pre-culture containing 100 ml fresh medium (B-CDM). The second pre-culture was incubated at 35° C. (+/−1° C.) and 150 rpm for 24 h (+/−1 h), and used to inoculate two shake flasks each containing 1L fresh medium (SS-cyclo for COQ467 and B-CDM for COQ365; see composition in Table 1). After growth at 35° C. (+/−1° C.) and 150 rpm for 40 h (+/−4 h), the two shake flasks from the third pre-culture were pooled. The pooled pre-culture was used to inoculate a fermentor as soon as the third pre-culture was stopped.

A 20L-fermentor (Biolafitte) was used. 10 L of medium ("SS cyclo" for COQ467 and "B-CDM" for COQ365) were aseptically transferred into the fermentor. The following conditions were used in order to set the 100%-dissolved oxygen (DO) level: temperature (35° C.) and head pressure (0.4 bar). Inoculation was achieved by the addition of 1.5 L of the pooled pre-culture.

During the fermentation, the temperature (35° C.), head pressure (0.4 bar), and air flow rate (20 L $min^{-1}$) were maintained constant. Foaming was controlled by automatic addition of a polydimethylsiloxane emulsion via a foam controller. The level of dissolved oxygen was set at 25% and regulated by increasing stirring when the DO fell below 25%. The minimum stirring speed was set at 50 rpm; the maximum stirring speed was set at 1,000 rpm. The pH was regulated at 7.2 by addition of phosphoric acid 50% (w/v) in COQ467 (SS-cyclo) and by addition of acetic acid 50% (w/v) in COQ365 (B-CDM).

During the fermentation, growth was monitored as optical density at 650 nm ($OD_{650\ nm}$) At the end of fermentation (defined as the time at which oxygen consumption decreases—as a consequence of glutamate exhaustion—, resulting in a decrease in stirring speed), pertussis toxin (PT) production in the culture supernatant was determined by Elisa. Table 2 compares the biomass yield, PT yield, and average generation time of fermentation COQ365 (B-CDM) and fermentation COQ467 (SS-cyclo).

Determination of PT concentration. PT concentration in culture supernatants was determined by enzyme-linked immunosorbent assay (ELISA). The wells of polystyrene microdilution plates (4-39454; Nunc) were coated overnight at 4° C. with 100 μl of purified polyclonal guinea pig anti-PT antiserum (1:16,000 dilution in 50 mM carbonate buffer pH 9.6). The plate was washed three times with DPBST (Dubelcco's phosphate buffered saline without Ca and Mg, containing 0.1% (v/v) Tween 20). Serial dilutions of purified PT standards and culture supernatants (in DPBST) were then added to each well (100 μl per well). After incubation for 30 minutes at room temperature, the plate was washed three times with DPBST. Goat anti-PT antiserum (1:500 dilution in DPBST) and anti-PT free guinea pig serum (1:1,000 dilution in DPBST) were then added to each well (100 μl per well). After incubation for 30 minutes at room temperature, the plate was washed three times with DPBST. Alkaline phosphatase-conjugated rabbit anti-goat immunoglobulin G (Zymed; 1:1,000 dilution in DPBST) was then added to each well (100 μl per well). After incubation for 30 minutes at room temperature, the plate was washed three times with DPBST. The plate was developed by adding a 10 g/L solution of p-nitrophenyl-phosphate (Calbiochem) in diethanolamine buffer (diethanolamine 9.7% (v/v), sodium azide 0.2 g/L, $MgCl_2.6H_2O$ 0.214 g/L, pH 9.8) to each well (100 µl per well). Color development was performed at room temperature, and stopped by adding 50 µl of NaOH 3M to each well. The absorbance of the wells was read at 405 nm within an hour after NaOH addition, using a Versamax microplate reader (Molecular Devices).

The B-CDM conditions resulted in higher growth yields and rates than SS-cyclo. PT production was also significantly increased. (See Table 2)

TABLE 1

Composition of SS and B-CDM media. All values in mg/L.

| Compound | Original SS | SS-cyclo | B-CDM |
|---|---|---|---|
| L-proline | 240 | 240 | 1040 |
| Na-L-glutamate | 10,720 | 10,700 | 20,000 |
| L-cystine | 40 | 0 | 0 |
| L-cysteine HCl | 0 | 40 | 40 |
| NaCl | 2,500 | 2,500 | 0 |
| $KH_2PO_4$ | 500 | 500 | 500 |
| KCl | 200 | 200 | 200 |
| $MgCl_2 \cdot 6H_2O$ | 100 | 100 | 100 |
| $CaCl_2 \cdot 2H_2O$ | 20 | 20 | 20 |
| $FeSO_4 \cdot 7H_2O$ | 10 | 10 | 10 |
| Tris | 6,075 | 1,820 | 6,100 |
| Ascorbic acid | 20 | 20 | 400 |
| Reduced glutathione (GSH) | 100 | 100 | 150 |
| niacin (nicotinic acid) | 4 | 4 | 4 |
| Dimethyl-β-cyclodextrin | 0 | 1,000 | 1,000 |
| L-alanine | 0 | 0 | 312 |
| L-Aspartic acid | 0 | 0 | 436 |
| L-Glutamic acid | 0 | 0 | 1,600 |
| L-histidine | 0 | 0 | 188 |
| L-glycine | 0 | 0 | 163 |
| L-isoleucine | 0 | 0 | 288 |
| L-leucine | 0 | 0 | 484 |
| L-lysine HCl | 0 | 0 | 600 |
| L-methionine | 0 | 0 | 156 |
| L-phenylalanine | 0 | 0 | 250 |
| L-serine | 0 | 0 | 230 |
| L-tyrosine | 0 | 0 | 67 |
| L-valine | 0 | 0 | 456 |

SS = Stainer & Scholte medium

B-CDM = Basic Chemically Defined Medium

Tris = tris(hydroxymethyl)aminomethane

TABLE 2

Main fermentation parameters for *B. pertussis* cultivated in SS-cyclo or in B-CDM

| | Medium | |
|---|---|---|
| | COQ365 B-CDM | COQ467 SS-cyclo |
| pH regulation | Acetic acid 50% (w/v) | Phosphoric acid 50% (w/v) |
| Initial biomass ($OD_{650nm}$)* | 0.149 | 0.138 |
| Final biomass ($OD_{650nm}$) | 9.20 | 1.75 |
| Biomass yield ($OD_{650nm}$)** | 9.05 | 1.61 |
| Total fermentation time*** | 41 h 14 | 63 h 00 |

TABLE 2-continued

Main fermentation parameters for *B. pertussis* cultivated in SS-cyclo or in B-CDM

| | Medium | |
|---|---|---|
| | COQ365 B-CDM | COQ467 SS-cyclo |
| Average generation time**** | 6.6 h | 17.2 h |
| Final PT concentration | 10 mg/L | 1 mg/L |

*Initial biomass concentration calculated based on measured $OD_{650nm}$ of the pre-culture, i.e. $1.5*OD_{pre-culture}/11.5$.

**Yield was calculated as the difference between $OD_{650nm}$ at the end of fermentation and $OD_{650nm}$ at the start of fermentation.

***The total fermentation time is defined as the time at which oxygen consumption decreases (as a consequence of glutamate exhaustion), resulting in a decrease in stirring speed.

****Average generation time calculated as follows. First, the number of generations is calculated as the ratio between $OD_{650nm}$ at the end of fermentation and $OD_{650nm}$ at the start of fermentation, converted to $log_2$. The average generation time is then calculated by dividing the total fermentation time by the number of generations.

EXAMPLE 2

Effect of the Iron Source on 20 L-scale Fermentation of *Bordetella pertussis* in Chemically Defined Medium Ferric citrate was evaluated as an alternative to ferrous sulfate in fermentation COQ348.

A first shake-flask pre-culture containing 7.5 ml fresh medium (B-CDM; see composition in Table 1) was inoculated with $10^9$ *B. pertussis* CFUs and incubated at 35° C. (+/−1° C.) and 150 rpm for 24 h (+/−1 h). The first pre-culture was used to inoculate a second shake-flask pre-culture containing 100 ml fresh medium (B-CDM). The second pre-culture was incubated at 35° C. (+/−1° C.) and 150 rpm for 24 h (+/−1 h), and used to inoculate two shake flasks each containing 1 L fresh medium (B-CDM modified to contain 10 mg/L Fe(III)-citrate trihydrate and no $FeSO_4$). After growth at 35° C. (+/−1° C.) and 150 rpm for 40 h (+/−4 h), the two shake flasks from the third pre-culture were pooled. The pooled pre-culture was used to inoculate a fermentor as soon as the third pre-culture was stopped.

A 20 L-fermentor (Biolafitte) was used. 10 L of medium (B-CDM modified to contain 10 mg/L Fe(III)-citrate trihydrate and no $FeSO_4$) were aseptically transferred into the fermentor. The following conditions were used in order to set the 100%-dissolved oxygen (DO) level: temperature (35° C.) and head pressure (0.4 bar). Inoculation was achieved by the addition of 1.5 L of the pooled pre-culture.

During the fermentation, the temperature (35° C.), head pressure (0.4 bar), and air flow rate (20 L $min^{-1}$) were maintained constant. Foaming was controlled by automatic addition of a polydimethylsiloxane emulsion via a foam controller. The level of dissolved oxygen was set at 25% and regulated by increasing stirring when the DO fell below 25%. The minimum stirring speed was set at 50 rpm; the maximum stirring speed was set at 1,000 rpm. The pH was regulated at 7.2 by addition of acetic acid 50% (w/v).

During the fermentation, growth was monitored as optical density at 650 nm ($OD_{650\ nm}$) At the end of fermentation (defined as the time at which oxygen consumption decreases—as a consequence of glutamate exhaustion—, resulting in a decrease in stirring speed), pertussis toxin (PT) production in the culture supernatant was determined by Elisa. Table 3 compares the biomass yield, PT yield, and average generation time of fermentation COQ352 (B-CDM modified to contain 10 mg/L Fe(III)-citrate trihydrate and no $FeSO_4$) and fermentation COQ365 (B-CDM with $FeSO_4$; see example 1).

The growth yield and rate were similar between the two conditions, in terms of maximum biomass concentration, indicating that inorganic sulfate can be omitted from medium composition, and that iron can be supplied either as Fe(II) or Fe(III) without affecting the growth of *B. pertussis*. PT production was also significantly increased when ferric citrate, rather than ferrous sulfate, was used as an iron source.

TABLE 3

Main fermentation parameters for *B. pertussis* cultivated in B-CDM containing 10 mg/L $FeSO_4$•$7H_2O$ (COQ365) or Fe(III)-citrate•$3H_2O$ (COQ352) as the sole source of iron

| | iron source | |
|---|---|---|
| | COQ365 10 mg/L $FeSO_4$•$7H_2O$ | COQ352 10 mg/L Fe(III)-citrate•$3H_2O$ |
| Initial biomass ($OD_{650nm}$)* | 0.149 | 0.163 |
| Final biomass ($OD_{650nm}$) | 9.20 | 9.75 |
| Biomass yield ($OD_{650nm}$)** | 9.05 | 9.59 |
| Total fermentation time*** | 41 h 14 | 42 h 45 |
| Average generation time**** | 6.9 h | 7.2 h |
| Final PT concentration | 10 mg/L | 16 mg/L |

*Initial biomass concentration calculated based on measured $OD_{650nm}$ of the pre-culture, i.e. 1.5*$OD_{pre\text{-}culture}$/11.5.
**Yield was calculated as the difference between $OD_{650nm}$ at the end of fermentation and $OD_{650nm}$ at the start of fermentation.
***The total fermentation time is defined as the time at which oxygen consumption decreases (as a consequence of glutamate exhaustion), resulting in a decrease in stirring speed.
****Average generation time calculated as follows. First, the number of generations is calculated as the ratio between $OD_{650nm}$ at the end of fermentation and $OD_{650nm}$ at the start of fermentation, converted to $log_2$. The average generation time is then calculated by dividing the total fermentation time by the number of generations.

EXAMPLE 3

Thiosulfate as a Source of Sulfur for Growth of *Bordetella pertussis*

Based on literature, growth of *B. pertussis* is only possible in the presence of an organic source of sulfur, which can be provided as cystine, cysteine, and/or glutathione (Jebb and Tomlinson (1957) J. Gen. Microbiol. 17:59).

Assays were performed in order to determine whether inorganic sources of sulfur were able to support growth of *B. pertussis*. A shake-flask containing 7.5 ml fresh medium (B-CDM modified to contain 0.604 g/L niacin) was inoculated with $10^9$ *B. pertussis* CFUs and incubated at 35° C. (+/−1° C.) and 150 rpm for 24 h (+/−5 h). Cells were harvested by centrifugation, washed twice with NaCl 0.9% (w/v), and resuspended in fresh medium containing no S source (see composition in Table 4) at a theoretical $OD_{650\ nm}$ of 0.5, as calculated from the $OD_{650\ nm}$ of the culture before harvest. 20 μl of this cell suspension were used to inoculate each well of a 96-well microtiter plate filled with 180 μl of fresh medium containing no S source (see composition in Table 4). To each of the wells, 20 μl of a supplement solution was added, which contained one of the compounds listed in Table 5. Only the inner wells of the plate were used for cultures, in order to minimize evaporation, and one control was included, in which the supplement solution was replaced with water. The plate was then incubated for 53 hours at 35° C. in a Biotek Synergy H1 reader with constant shaking, and growth was automatically monitored every 10 minutes as $OD_{650\ nm}$. Results of the growth assay are shown in Table 5.

Inorganic sulfate and sulfite were not able to support growth of *B. pertussis*. However, growth was observed in the presence of thiosulfate as the sole source of sulfur in the medium. These results demonstrate i) that sulfate can be omitted from the medium, and ii) that an organic source of sulfur such as cystine, cysteine, or glutathione does not need to be present, provided a compounds which supports growth such as thiosulfate is present.

TABLE 4

Composition of chemically defined medium used to screen for potential inorganic sources of sulfur.

| Compound | Concentration (mg/L) |
|---|---|
| Na-L-glutamate | 5000 |
| NaCl | 4650 |
| $KH_2PO_4$ | 500 |
| KCl | 200 |
| $MgCl_2$•$6H_2O$ | 100 |
| $CaCl_2$•$2H_2O$ | 20 |
| Fe(III)-citrate•$3H_2O$ | 10 |
| Tris | 6100 |
| niacin (nicotinic acid) | 4 |
| Dimethyl-β-cyclodextrin | 1000 |

TABLE 5

Growth of *B. pertussis* in the presence of different sources of sulfur.

| Sulfur source | Concentration in medium | Biomass yield after 53 h* | Growth** |
|---|---|---|---|
| none (negative control) | N/A | 0.017 | − |
| L-cysteine | 27 mM | 0.512 | + |
| disodium sulfate | 12 mM | 0.015 | − |
| disodium sulfite | 12 mM | 0.007 | |
| disodium sulfite | 1 mM | 0.011 | − |
| disodium thiosulfate | 12 mM | 0.472 | + |
| disodium thiosulfate | 1 mM | 0.227 | + |

*calculated as the difference between $OD_{650nm}$ after 53 h and the initial $OD_{650nm}$
**+, biomass yield higher than negative control; −, biomass yield lower than or equal to the negative control

EXAMPLE 4

Screening for Alternative Buffers in Chemically Defined Medium

A screening was performed for alternatives to Tris buffer in the B-CDM medium. A first shake-flask pre-culture containing 7.5 ml fresh medium (B-CDM) was inoculated with $10^9$ *B. pertussis* CFUs and incubated at 35° C. (+/−1° C.) and 150 rpm for 24 h (+/−1 h). The first pre-culture was used to inoculate a second shake-flask pre-culture containing 100 ml fresh medium (B-CDM). The second pre-culture was incubated at 35° C. (+/−1° C.) and 150 rpm for 24 h (+/−1 h). Cells were then harvested by centrifugation, washed in NaCl 0.9%, and resuspended in NaCl 0.9%.This cell suspension was used to inoculate a set of 9 shake-flasks, each containing 50 ml of fresh medium (B-CDM) or with a medium in which the tris buffer in CDM was replaced with another buffer as listed in Table 6. The flasks were incubated at 35° C. and 150 rpm for 48 h. Growth was monitored as $OD_{650\ nm}$ after 24 h and 48 h. Results are presented in Table 6.

Both β-glycerophosphate and MOPS were able to support growth of *B. pertussis* in B-CDM. Globally, MOPS was superior to β-glycerophosphate in terms of growth rate (biomass yield after 24 h) and yield (biomass yield after 48 h). With both buffers, lower concentrations resulted in faster growth and higher final biomass yield. At the lowest concentration tested (2.5 g/L), MOPS showed a beneficial effect on growth rate (biomass yield after 24 h), compared to the control conditions using Tris as a buffer.

TABLE 6

Growth of *B. pertussis* in B-CDM in the presence of different buffers

| Buffer | Buffer concentration | Relative biomass yield after 24 h* | Relative biomass yield after 48 h* |
|---|---|---|---|
| Tris | 6.1 g/L | 100% | 100% |
| β-glycerophosphate | 2.5 g/L | 88% | 79% |
| β-glycerophosphate | 5.0 g/L | 89% | 67% |
| β-glycerophosphate | 10.0 g/L | 68% | 59% |
| β-glycerophosphate | 20.0 g/L | 46% | 45% |
| MOPS | 2.5 g/L | 114% | 91% |
| MOPS | 5.0 g/L | 85% | 88% |
| MOPS | 10.0 g/L | 111% | 84% |
| MOPS | 20.0 g/L | 81% | 76% |

*The biomass yield is expressed relative to the control conditions (Tris buffer) at the same time of incubation

EXAMPLE 5

Impact of $Cu^{2+}$ Addition on 20 L-scale Fermentation of *Bordetella pertussis* in Chemically Defined Medium The effect of $Cu^{2+}$ supplementation was evaluated in fermentation COQ348.

A first shake-flask pre-culture containing 7.5 ml fresh medium (B-CDM; see composition in Table 1) was inoculated with $10^9$ *B. pertussis* CFUs and incubated at 35° C. (+/−1° C.) and 150 rpm for 24 h (+/−1 h). The first pre-culture was used to inoculate a second shake-flask pre-culture containing 100 ml fresh medium (B-CDM). The second pre-culture was incubated at 35° C. (+/−1° C.) and 150 rpm for 24 h (+/−1 h), and used to inoculate two shake flasks each containing 1 L fresh medium (B-CDM supplemented with 1.28 mg/L (7.5 μM) $CuCl_2.2H_2O$). After growth at 35° C. (+/−1° C.) and 150 rpm for 40 h (+/−4 h), the two shake flasks from the third pre-culture were pooled. The pooled pre-culture was used to inoculate a fermentor as soon as the third pre-culture was stopped. A 20 L-fermentor Biolafitte) was used. 10 L of medium (B-CDM supplemented with 1.28 mg/L (7.5 μM) $CuCl_2.2H_2O$) were aseptically transferred into the fermentor. The following conditions were used in order to set the 100%-dissolved oxygen (DO) level: temperature (35° C.) and head pressure (0.4 bar). Inoculation was achieved by the addition of 1.5 L of the pooled pre-culture. During the fermentation, the temperature (35° C.), head pressure (0.4 bar), and air flow rate (20 L $min^{-1}$) were maintained constant. Foaming was controlled by automatic addition of a polydimethylsiloxane emulsion via a foam controller. The level of dissolved oxygen was set at 25% and regulated by increasing stirring when the DO fell below 25%. The minimum stirring speed was set at 50 rpm; the maximum stirring speed was set at 1,000 rpm. The pH was regulated at 7.2 by addition of acetic acid 50% (w/v).

During the fermentation, growth was monitored as optical density at 650 nm ($OD_{650\ nm}$). At the end of fermentation (defined as the time at which oxygen consumption decreases—as a consequence of glutamate exhaustion—, resulting in a decrease in stirring speed), pertussis toxin (PT) production in the culture supernatant was determined by Elisa. Table 7 compares the biomass yield, PT yield, and average generation time of fermentation COQ348 (B-CDM with Cu supplementation) and fermentation COQ365 (B-CDM without Cu supplementation; see example 1).

The addition of $CuCl_2$ to the chemically defined medium resulted in a significant increase in biomass yield. The growth rate and PT yield were also positively affected.

TABLE 7

Main fermentation parameters for *B. pertussis* cultivated in B-CDM with or without $Cu^{2+}$ supplementation

| | COQ365 | COQ348 |
|---|---|---|
| Added $CuCl_2$•$2H_2O$ | 0 mg/L | 1.28 mg/L |
| Initial biomass ($OD_{650nm}$)* | 0.149 | 0.183 |
| Final biomass ($OD_{650nm}$) | 9.20 | 10.90 |
| Biomass yield ($OD_{650nm}$)** | 9.05 | 10.72 |
| Total fermentation time*** | 41 h 14 | 37 h 00 |
| Average generation time**** | 6.9 h | 6.3 h |
| Final PT concentration | 10 mg/L | 11 mg/L |

*Initial biomass concentration calculated based on measured $OD_{650nm}$ of the pre-culture, i.e. 1.5*$OD_{pre\text{-}culture}$/11.5.
**Yield was calculated as the difference between $OD_{650nm}$ at the end of fermentation and $OD_{650nm}$ at the start of fermentation.
***The total fermentation time is defined as the time at which oxygen consumption decreases (as a consequence of glutamate exhaustion), resulting in a decrease in stirring speed.
****Average generation time calculated as follows. First, the number of generations is calculated as the ratio between $OD_{650nm}$ at the end of fermentation and $OD_{650nm}$ at the start of fermentation, converted to $log_2$. The average generation time is then calculated by dividing the total fermentation time by the number of generations.

EXAMPLE 6

20 L-scale Fermentation of *Bordetella pertussis* in Improved Chemically Defined Medium An improved formulation of the basic CDM (B-CDM) was evaluated in fermentation COQ426.

A first shake-flask pre-culture containing 7.5 ml fresh medium (B-CDM; see composition in Table 1) was inoculated with $10^9$ *B. pertussis* CFUs and incubated at 35° C. (+/−1° C.) and 150 rpm for 24 h (+/−1 h). The first pre-culture was used to inoculate a second shake-flask pre-culture containing 100 ml fresh medium (B-CDM). The second pre-culture was incubated at 35° C. (+/−1° C.) and 150 rpm for 24 h (+/−1 h), and used to inoculate two shake flasks each containing 1 L fresh medium (Improved CDM; see composition in Table 8). After growth at 35° C. (+/−1° C.) and 150 rpm for 40 h (+/−4 h), the two shake flasks from the third pre-culture were pooled. The pooled pre-culture was used to inoculate a fermentor as soon as the third pre-culture was stopped. A 20 L-fermentor (Biolafitte) was used. 10 L of medium were aseptically transferred into the fermentor. The following conditions were used in order to set the 100%-dissolved oxygen (DO) level: temperature (35° C.) and head pressure (0.4 bar). Inoculation was achieved by the addition of 1.5 L of the pooled pre-culture. During the fermentation, the temperature (35° C.), head pressure (0.4 bar), and air flow rate (20 L $min^{-1}$) were maintained constant. Foaming was controlled by automatic addition of a polydimethylsiloxane emulsion via a foam controller. The level of dissolved oxygen was set at 25% and regulated by increasing stirring when the DO fell below 25%. The minimum stirring speed was set at 50 rpm; the maximum stirring speed was set at 1,000 rpm. The pH was regulated at 7.2 by addition of phosphoric acid 50% (w/v).

During the fermentation, growth was monitored as optical density at 650 nm ($OD_{650\ nm}$). At the end of fermentation (defined as the time at which oxygen consumption decreases—as a consequence of glutamate exhaustion—, resulting in a decrease in stirring speed), pertussis toxin (PT) production in the culture supernatant was determined by Elisa.

Table 9 compares the biomass yield, PT yield, and average generation time of fermentation COQ426 (Improved CDM) and fermentation COQ365 (B-CDM; see example 1).

The Improved CDM conditions resulted in a slightly lower growth yield compared to the basic CDM. The growth rate was also slightly lower. However, PT production was dramatically increased (+170%).

TABLE 8

Composition of B-CDM and Improved CDM. All values in mg/L.

| Compound | B-CDM | Improved CDM |
|---|---|---|
| L-proline | 1,040 | 882 |
| Na-L-glutamate | 20,000 | 18,677 |
| L-cysteine HCl | 40 | 4 |
| NaCl | 2,500 | 73 |
| $KH_2PO_4$ | 500 | 500 |
| KCl | 200 | 200 |
| $MgCl_2$•$6H_2O$ | 100 | 1,000 |
| $CaCl_2$•$2H_2O$ | 20 | 20 |
| $FeSO_4$•$7H_2O$ | 10 | 0 |
| Fe(III)-citrate•$3H_2O$ | 0 | 20 |
| Tris | 6,100 | 0 |
| $CuCl_2$•$2H_2O$ | 0 | 1.28 |
| $CoCl_2$•$6H_2O$ | 0 | 0.42 |
| $ZnCl_2$ | 0 | 10 |
| MOPS | 0 | 2,500 |
| Ascorbic acid | 400 | 623 |
| Reduced glutathione (GSH) | 150 | 233 |
| niacin (nicotinic acid) | 4 | 6 |
| Dimethyl-β-cyclodextrin | 1,000 | 1,000 |
| Na acetate | 0 | 409 |
| L-alanine | 312 | 304 |
| L-Aspartic acid | 436 | 524 |
| L-Glutamic acid | 1,600 | 3,475 |
| L-histidine | 188 | 32 |
| L-glycine | 163 | 149 |
| L-isoleucine | 288 | 244 |
| L-leucine | 484 | 438 |
| L-lysine HCl | 600 | 393 |
| L-methionine | 156 | 116 |
| L-phenylalanine | 250 | 234 |
| L-serine | 230 | 187 |
| L-tyrosine | 67 | 34 |
| L-valine | 456 | 399 |
| thiamine HCl | 0 | 10 |
| biotin | 0 | 0.2 |
| riboflavin | 0 | 0.3 |
| calcium pantothenate | 0 | 4 |

TABLE 9

Main fermentation parameters for *B. pertussis* cultivated in B-CDM or in Improved CDM

| | Medium | |
|---|---|---|
| | COQ365 B-CDM | COQ426 Improved CDM |
| Initial biomass ($OD_{650nm}$)* | 0.149 | 0.143 |
| Final biomass ($OD_{650nm}$) | 9.20 | 8.30 |
| Biomass yield ($OD_{650nm}$)** | 9.05 | 8.15 |
| Total fermentation time*** | 41 h 14 | 46 h 30 |
| Average generation time**** | 6.9 h | 7.9 h |
| Final PT concentration | 10 mg/L | 27 mg/L |

TABLE 9-continued

*Initial biomass concentration calculated based on measured $OD_{650nm}$ of the pre-culture, i.e. 1.5*$OD_{pre\text{-}culture}$/11.5.
**Yield was calculated as the difference between $OD_{650nm}$ at the end of fermentation and $OD_{650nm}$ at the start of fermentation.
***The total fermentation time is defined as the time at which oxygen consumption decreases (as a consequence of glutamate exhaustion), resulting in a decrease in stirring speed.
****Average generation time calculated as follows. First, the number of generations is calculated as the ratio between $OD_{650nm}$ at the end of fermentation and $OD_{650nm}$ at the start of fermentation, converted to $\log_2$. The average generation time is then calculated by dividing the total fermentation time by the number of generations.

EXAMPLE 7

20 L-scale Fermentation of *Bordetella pertussis* in Improved Chemically Defined Medium Containing Thiosulfate as a Source of Sulfur A modified formulation of the Improved CDM (example 6) was evaluated in fermentation COQ454. In this medium, cysteine was replaced with thiosulfate as a source of sulfur.

A first shake-flask pre-culture containing 7.5 ml fresh medium (B-CDM; see composition in Table 1) was inoculated with $10^9$ *B. pertussis* CFUs and incubated at 35° C. (+/−1° C.) and 150 rpm for 24 h (+/−1 h). The first pre-culture was used to inoculate a second shake-flask pre-culture containing 100 ml fresh medium (B-CDM). The second pre-culture was incubated at 35° C. (+/−1° C.) and 150 rpm for 24 h (+/−1 h), and used to inoculate two shake flasks each containing 1 L fresh medium (Improved CDM with thiosulfate; see composition in Table 10). After growth at 35° C. (+/−1° C.) and 150 rpm for 40 h (+/−4 h), the two shake flasks from the third pre-culture were pooled. The pooled pre-culture was used to inoculate a fermentor as soon as the third pre-culture was stopped. A 20 L-fermentor (Biolafitte) was used. 10 L of medium were aseptically transferred into the fermentor. The following conditions were used in order to set the 100%-dissolved oxygen (DO) level: temperature (35° C.) and head pressure (0.4 bar). Inoculation was achieved by the addition of 1.5 L of the pooled pre-culture.

During the fermentation, the temperature (35° C.), head pressure (0.4 bar), and air flow rate (20 L $min^{-1}$) were maintained constant. Foaming was controlled by automatic addition of a polydimethylsiloxane emulsion via a foam controller. The level of dissolved oxygen was set at 25% and regulated by increasing stirring when the DO fell below 25%. The minimum stirring speed was set at 50 rpm; the maximum stirring speed was set at 1,000 rpm. The pH was regulated at 7.2 by addition of phosphoric acid 50% (w/v).

During the fermentation, growth was monitored as optical density at 650 nm ($OD_{650\ nm}$). At the end of fermentation (defined as the time at which oxygen consumption decreases—as a consequence of glutamate exhaustion—, resulting in a decrease in stirring speed), pertussis toxin (PT) production in the culture supernatant was determined by Elisa. Table 11 compares the biomass yield, PT yield, and average generation time of fermentation COQ454 (Improved CDM with thiosulfate), fermentation COQ426 (Improved CDM; see example 6), and fermentation COQ365 (B-CDM; see example 1).

The biomass yield in "Improved CDM with thiosulfate" was slightly lower compared to the basic CDM, but resulted in a higher growth rate and higher PT production (+310%). Compared to the "Improved CDM", the "Improved CDM with thiosulfate" medium resulted in a similar biomass yield, higher growth rate, and higher PT production (+52%).

TABLE 10

Composition of B-CDM, Improved CDM, and Improved CDM with thiosulfate. All values in mg/L.

| Compound | B-CDM | Improved CDM | Improved CDM with thiosulfate |
|---|---|---|---|
| L-proline | 1,040 | 882 | 882 |
| Na-L-glutamate | 20,000 | 18,677 | 18,677 |
| L-cysteine HCl | 40 | 4 | 0 |
| Sodium thiosulfate | 0 | 0 | 2.83 |
| NaCl | 2,500 | 73 | 73 |
| $KH_2PO_4$ | 500 | 500 | 500 |
| KCl | 200 | 200 | 200 |
| $MgCl_2$•$6H_2O$ | 100 | 1,000 | 1,000 |
| $CaCl_2$•$2H_2O$ | 20 | 20 | 20 |
| $FeSO_4$•$7H_2O$ | 10 | 0 | 0 |
| Fe(III)-citrate•$3H_2O$ | 0 | 20 | 20 |
| Tris | 6,100 | 0 | 0 |
| $CuCl_2$•$2H_2O$ | 0 | 1.28 | 1.28 |
| $CoCl_2$•$6H_2O$ | 0 | 0.42 | 0.42 |
| $ZnCl_2$ | 0 | 10 | 10 |
| MOPS | 0 | 2,500 | 2,500 |
| Ascorbic acid | 400 | 623 | 623 |
| Reduced glutathione (GSH) | 150 | 233 | 233 |
| niacin (nicotinic acid) | 4 | 6 | 6 |
| Dimethyl-β-cyclodextrin | 1,000 | 1,000 | 1,000 |
| Na acetate | 0 | 409 | 409 |
| L-alanine | 312 | 304 | 304 |
| L-Aspartic acid | 436 | 524 | 524 |
| L-Glutamic acid | 1,600 | 3,475 | 3,475 |
| L-histidine | 188 | 32 | 32 |
| L-glycine | 163 | 149 | 149 |
| L-isoleucine | 288 | 244 | 244 |
| L-leucine | 484 | 438 | 438 |
| L-lysine HCl | 600 | 393 | 393 |
| L-methionine | 156 | 116 | 116 |
| L-phenylalanine | 250 | 234 | 234 |
| L-serine | 230 | 187 | 187 |
| L-tyrosine | 67 | 34 | 34 |
| L-valine | 456 | 399 | 399 |
| thiamine HCl | 0 | 10 | 10 |
| biotin | 0 | 0.2 | 0.2 |
| riboflavin | 0 | 0.3 | 0.3 |
| calcium pantothenate | 0 | 4 | 4 |

TABLE 11

Main fermentation parameters for *B. pertussis* cultivated in B-CDM, in Improved CDM, or in Improved CDM with thiosulfate

| | Medium | | |
|---|---|---|---|
| | COQ365 B-CDM | COQ426 Improved CDM | COQ454 Improved CDM with thiosulfate |
| Initial biomass ($OD_{650nm}$)* | 0.149 | 0.143 | 0.157 |
| Final biomass ($OD_{650nm}$) | 9.20 | 8.30 | 8.30 |
| Biomass yield ($OD_{650nm}$)** | 9.05 | 8.15 | 8.14 |
| Total fermentation time*** | 41 h 14 | 46 h 30 | 41 h 15 |
| Average generation time**** | 6.9 h | 7.9 h | 7.2 h |
| Final PT concentration | 10 mg/L | 27 mg/L | 41 mg/L |

TABLE 11-continued

*Initial biomass concentration calculated based on measured $OD_{650nm}$ of the pre-culture, i.e. 1.5*$OD_{pre\text{-}culture}$/11.5.

**Yield was calculated as the difference between $OD_{650nm}$ at the end of fermentation and $OD_{650nm}$ at the start of fermentation.

***The total fermentation time is defined as the time at which oxygen consumption decreases (as a consequence of glutamate exhaustion), resulting in a decrease in stirring speed.

****Average generation time calculated as follows. First, the number of generations is calculated as the ratio between $OD_{650nm}$ at the end of fermentation and $OD_{650nm}$ at the start of fermentation, converted to $log_2$. The average generation time is then calculated by dividing the total fermentation time by the number of generations.

EXAMPLE 8

Growth of *B. pertussis* in Minimal Media Containing Only One Amino Acid

Assays were performed in order to determine whether growth of *B. pertussis* is possible in minimal media containing a single amino acid as the sole source of carbon and nitrogen. A shake-flask containing 7.5 ml fresh medium (B-CDM containing 0.604 g/L niacin) was inoculated with $10^9$ *B. pertussis* CFUs and incubated at 35° C. (+/−1° C.) and 150 rpm for 24 h (+/−5 h). Cells were harvested by centrifugation, washed twice with NaCl 0.9% (w/v), and resuspended in fresh medium (see composition in Table 12) at a theoretical $OD_{650\ nm}$ of 0.5, as calculated from the $OD_{650\ nm}$ of the culture before harvest. 1 ml of this cell suspension was used to inoculate shake-flasks containing 30 ml of the medium in Table 12, supplemented with a single amino acid (L-cysteine 125 mM, L-proline 125 mM, L-glutamate 125 mM, L-glutamine 125 mM, L-aspartate 30 mM, L-asparagine 125 mM, L-serine 125 mM, or L-alanine 125 mM) as a source of C and N, and thiosulfate 0.25 mM as a source of S (except for L-Cys supplementation, where no thiosulfate was added). The same medium with ammonium chloride (25 mM) and thiosulfate (0.25 mM), but no amino acid, was used as a negative control. The shake flasks were then incubated for approximately 10 days at 35° C. under constant shaking (150 rpm). Growth was monitored as $OD_{650\ nm}$. Results of the growth assay are shown in FIG. 1.

All tested amino acids were able to support growth of *B. pertussis* as the sole source of C and N, provided a source of S was present (thiosulfate). When L-Cys was used as an amino acid, no additional source of sulfur was required.

TABLE 12

Composition of chemically defined medium used to assay growth on single amino acids.

| Compound | Concentration (mg/L) |
|---|---|
| NaCl | 7,148 |
| $KH_2PO_4$ | 500 |
| KCl | 200 |
| $MgCl_2$•$6H_2O$ | 1,000 |
| $CaCl_2$•$2H_2O$ | 100 |
| Fe(III)-citrate•$3H_2O$ | 20 |

TABLE 12-continued

Composition of chemically defined medium used to assay growth on single amino acids.

| Compound | Concentration (mg/L) |
|---|---|
| MOPS | 2,500 |
| niacin (nicotinic acid) | 6 |
| Dimethyl-β-cyclodextrin | 1,000 |
| $CuCl_2$•$2H_2O$ | 1.28 |
| $CoCl_2$•$6H_2O$ | 0.42 |
| $ZnCl_2$ | 10 |
| biotin | 0.2 |
| riboflavin | 0.3 |
| calcium pantothenate | 4 |

EXAMPLE 9

Growth of *B. Pertussis* in Minimal Media Containing No Amino Acid

Figure 2:
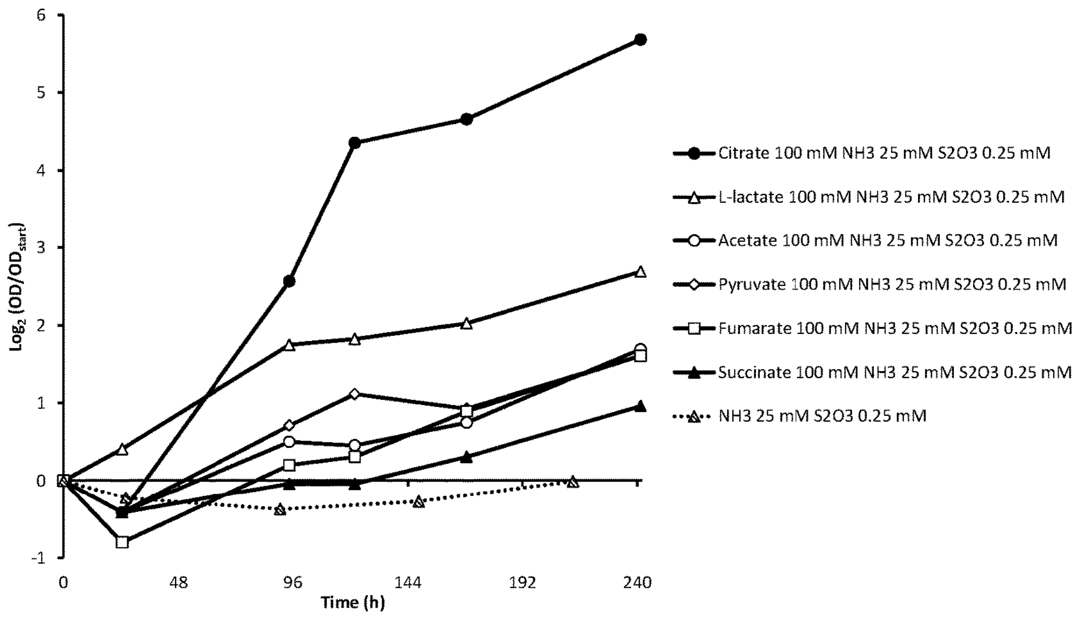

Assays were performed in order to determine whether growth of *B. pertussis* is possible in minimal media in which nitrogen was provided solely as inorganic ammonia, sulfur as thiosulfate, and carbon as an organic acid. A shake-flask containing 7.5 ml fresh medium (B-CDM containing 0.604 g/L niacin) was inoculated with $10^9$ *B. pertussis* CFUs and incubated at 35° C. (+/−1° C.) and 150 rpm for 24 h (+/−5 h). Cells were harvested by centrifugation, washed twice with NaCl 0.9% (w/v), and resuspended in fresh medium (see composition in Table 13) at a theoretical $OD_{650\ nm}$ of 0.5, as calculated from the $OD_{650\ nm}$ of the culture before harvest. 1 ml of this cell suspension was used to inoculate shake-flasks containing 30 ml of the medium in Table 13, supplemented with a single organic acid (citrate 100 mM, L-lactate 100 mM, acetate 100 mM, pyruvate 100 mM, fumarate 100 mM, or succinate 100 mM). The same medium with no organic acid supplement, was used as a negative control. The shake flasks were then incubated for approximately 10 days at 35° C. under constant shaking (150 rpm). Growth was monitored as $OD_{650\ nm}$. Results of the growth assay are shown in FIG. 2.

All tested organic acids were able to support growth of *B. pertussis* as the sole source of C.

TABLE 13

Composition of chemically defined medium used to assay growth in the absence of amino acids

| Compound | Concentration (mg/L) |
|---|---|
| $KH_2PO_4$ | 500 |
| KCl | 200 |
| $MgCl_2$•$6H_2O$ | 1,000 |
| $CaCl_2$•$2H_2O$ | 100 |
| Fe(III)-citrate•$3H_2O$ | 20 |
| MOPS | 2,500 |
| niacin (nicotinic acid) | 6 |
| Dimethyl-β-cyclodextrin | 1,000 |
| $CuCl_2$•$2H_2O$ | 1.28 |
| $CoCl_2$•$6H_2O$ | 0.42 |
| $ZnCl_2$ | 10 |
| biotin | 0.2 |
| riboflavin | 0.3 |
| calcium pantothenate | 4 |
| Ammonium chloride | 1,337 |
| Sodium thiosulfate | 62 |

What is claimed is:

1. A chemically defined medium for the industrial scale culture of a species of *Bordetella* comprising:

(i) an iron component selected from the group consisting of Fe(II) complexed to an organic compound and Fe(III) complexed to an organic compound, where the organic compound is selected from heme, haemoglobin, myoglobin, transferrin, ferritin, lactoferrin, enterobactin, aerobactin, alcaligin, coprogen, ferrichrome, desferrioxamine, ferroxamine, hydroxamate, citrate and dihydroxybenzoylserine;

(ii) 3-(N-morpholino)propanesulfonic acid (MOPS);

(iii) dimethyl-β-cyclodextrin; and (iv) an amino acid selected from the group consisting of aspartate at a concentration 1000 μM or greater, glycine at a concentration of 1000 μM or greater, methionine at a concentration of 500 μM or greater and leucine at a concentration of 1500 μM or greater, wherein said chemically defined medium does not comprise FeSO4 or tris(hydroxymethyl)aminomethane.

2. A chemically defined medium according to claim 1, further comprising a component selected from the group consisting of:

(i) 2 μM or greater copper;

(ii) 2 μM or greater magnesium;

(iii) an additive selected from the group consisting of zinc, cobalt, thiamine, riboflavin and pantothenate; and (iv) an additive selected from the group consisting of 0.4 μM or greater biotin, 50 μM or greater calcium, 15 μM or greater niacin, and 25 μM or greater ascorbic acid.

3. A chemically defined medium according to claim 1, further comprising an inorganic source of sulphur selected from the group consisting of thiosulfate, trithionate, tetrathionate, peroxodisulfate, sulphide and sulphite, and wherein said medium does not comprise an organic source of sulfur.

4. The chemically defined medium according to claim 3 comprising greater than 0.005 mM thiosulfate.

5. The chemically defined medium according to claim 3 comprising greater than 0.003 mM trithionate.

6. The chemically defined medium according to claim 3 comprising greater than 0.002 mM tetrathionate.

7. The chemically defined medium according to claim 3 comprising greater than 0.005 mM peroxodisulfate.

8. The chemically defined medium according to claim 3 comprising greater than 0.010 mM sulphide.

9. The chemically defined medium according to claim 3 comprising greater than 0.010 mM sulphite.

10. The chemically defined medium of claim 1 comprising MOPS at a concentration of greater than 2 mM.

11. The chemically defined medium according to claim 1, further comprising copper in the form of copper chloride.

12. The chemically defined medium according to claim 1, further comprising an inorganic source of nitrogen selected from an ammonium salt and ammonium chloride.

13. The chemically defined medium according to claim 1, further comprising a source of carbon selected from the group consisting of glutamate, proline, citrate, lactate, acetate, pyruvate, fumarate and succinate.

14. The chemically defined medium according to claim 1, further comprising a component selected from the group consisting of:

(i) greater than 0.1 μM zinc;

(ii) greater than 0.05 μM cobalt;

(iii) greater than 100 μM calcium;

(iv) greater than 20 μM niacin;

(v) greater than 50 μM ascorbic acid;

(vi) greater than 0.1 μM thiamine;

(vii) greater than 0.4 μM biotin;

(viii) greater than 0.1 μM riboflavin; and (ix) greater than 0.1 μM pantothenate.

15. The chemically defined medium according to claim 1 further comprising an amino acid selected from the group consisting of:

(i) glutamate at a concentration of greater than 50 mM;

(ii) alanine at a concentration of greater than 1000 μM;

(iii) phenylalanine at a concentration of greater than 500 μ;

(iv) histidine at a concentration of greater than 50 μM;

(v) isoleucine at a concentration of greater than 500 μM;

(vi) lysine at a concentration of greater than 500 μM;

(vii) proline at a concentration of greater than 1000 μM;

(viii) serine at a concentration of greater than 500 μM;

(ix) valine at a concentration of greater than 1000 μM; and (x) tyrosine at a concentration of greater than 25 μM.

16. The chemically defined medium according to claim 1 further comprising glutathione at a concentration of greater than 100 μM.

17. The chemically defined medium according to claim 1 further comprising a component selected from the group consisting of:

(i) chloride at a concentration of less than 45 mM;

(ii) acetate at a concentration of greater than 1 mM; and (iii) potassium at a concentration of greater than 1 mM.

18. A fermentation process for growing a species of *Bordetella* in a chemically defined medium (CDM) comprising (a) inoculating a chemically defined medium according to claim 1 with a species of *Bordetella*; and (b) maintaining the species of *Bordetella* in the chemically defined medium for a period of time sufficient to allow biomass accumulation.

* * * * *